United States Patent
Li

(10) Patent No.: US 10,155,008 B2
(45) Date of Patent: Dec. 18, 2018

(54) USE OF 15 MALE FERTILITY RELATED PROTEINS OR COMBINATION THEREOF

(71) Applicant: YANTAI JUJIE BIOENGINEERING LIMITED COMPANY, Yantai, Shandong (CN)

(72) Inventor: Jianyuan Li, Shandong (CN)

(73) Assignee: YANTAI JUJIE BIOENGINEERING LIMITED COMPANY, Yantai, Shandong (CN)

( * ) Notice: Subject to any disclaimer, the term of this patent is extended or adjusted under 35 U.S.C. 154(b) by 0 days.

(21) Appl. No.: 15/304,992

(22) PCT Filed: Apr. 18, 2014

(86) PCT No.: PCT/CN2014/075726
§ 371 (c)(1),
(2) Date: Oct. 18, 2016

(87) PCT Pub. No.: WO2015/158006
PCT Pub. Date: Oct. 22, 2015

(65) Prior Publication Data
US 2017/0182083 A1    Jun. 29, 2017

(51) Int. Cl.
| | | |
|---|---|---|
| A61K 31/7105 | (2006.01) | |
| A61K 38/51 | (2006.01) | |
| G01N 33/68 | (2006.01) | |
| A61K 39/395 | (2006.01) | |
| G01N 33/53 | (2006.01) | |

(52) U.S. Cl.
CPC .......... *A61K 31/7105* (2013.01); *A61K 38/51* (2013.01); *A61K 39/39533* (2013.01); *C12Y 406/01001* (2013.01); *G01N 33/5308* (2013.01); *G01N 33/689* (2013.01); *A61K 2121/00* (2013.01); *G01N 2800/367* (2013.01)

(58) Field of Classification Search
None
See application file for complete search history.

(56) References Cited

FOREIGN PATENT DOCUMENTS

| | | |
|---|---|---|
| CN | 102262159 | 11/2011 |
| WO | 2010025548 | 3/2010 |

OTHER PUBLICATIONS

International search report for application No. PCT/CN2014/075726, dated Jan. 23, 2015 (4 pages, including English translation).

*Primary Examiner* — J. E. Angell
(74) *Attorney, Agent, or Firm* — Hamre, Schumann, Mueller & Larson, P.C.

(57) ABSTRACT

The present invention provides the use of the gene or protein of adenylate kinase 6 (AK6) or the combination of AK6 and other 14 genes or proteins related to male infertility for (i) preparing the agent or kit for detecting male infertility; and/or (ii) preparing the pharmaceutical composition for contraception.

8 Claims, 5 Drawing Sheets
Specification includes a Sequence Listing.

USE OF 15 MALE FERTILITY RELATED PROTEINS OR COMBINATION THEREOF

TECHNICAL FIELD

The application relates to the field of biological technology and medicine, in particular, to 15 age-related human sperm localization proteins for use in the diagnosis or treatment of male infertility.

BACKGROUND

Male infertility is one of the major factors causing infertility. According to the report of the World Health Organization (WHO) in 2,000, the global infertility rate was about 15%, in which male factors accounted for about 50%. Infertility rate in some countries in Europe is up to 30%. There are complex and various factors for male infertility, including abnormal and dysfunction of many factors, such as anatomy structure and function of the reproductive system, hormone regulation, the genetic material, and infection immunity.

Male infertility is not an independent disease, but resulted from the synthetic action of various diseases or multiple factors. Although the causes for male infertility are quite complex, the methods for routine semen detection are very limited at present.

Researches have shown that most reasons for male infertility are abnormal spermiogenesis or azoospermia. Sperms generated from human testis enter into the epididymis, be incubated and matured in the epididymis, while the function of sperms is gradually declined or even completely losted with the aging process.

A lot of studies about the function and regulation of the epididymis and testis are reported, however, so far, little has been known about the proteins (especially sperm localization proteins) expression pattern for the epididymis and testis from development to aging, not to mention the corresponding specific detection method. Therefore, it is urgent to seek male fertility-associated proteins which cause sperm aging and reduced fertility.

SUMMARY OF INVENTION

A use of a group of age-related, male fertility-associated proteins and the combination thereof for diagnosing or treating male infertility is provided by the present invention.

In the first aspect of the invention, a use of an adenylate kinase 6 (AK6) gene or protein thereof, or in combination with other male fertility-associated genes or proteins is provided, for preparing (i) a reagent or a kit for detecting male infertility; and/or (ii) a pharmaceutical composition for contraception.

In another preferred embodiment, said other male fertility-associated proteins comprise one or more proteins listed in Table 1.

In another preferred embodiment, said other male fertility-associated proteins further comprise one or more male fertility-associated proteins described in the Chinese patent No. CN201010195377.9.

In another preferred embodiment, an adenylate kinase 6 (AK6) gene or protein thereof, or in combination with other male fertility-associated genes or proteins is further used for evaluating cell qualities.

In another preferred embodiment, the combination comprise AK6 in combination with 1, 2, 3, 4, 5, 6, 7, 8, 9, 10, 11, 12, 13 or 14 proteins listed in Table 1.

In another preferred embodiment, the reagent further comprises the detecting reagent for detecting one or more proteins or genes selected from Table 1.

In another preferred embodiment, the detecting reagent comprises AK6 and/or one or more antibodies, antisense RNA, microRNA, siRNA, shRNA, and activity inhibitors thereof selected from the proteins or genes thereof listed in Table 1, for example, inhibitors of AK6.

In another preferred embodiment, the inhibitors of AK6 comprise antibodies of AK6, antisense RNAs of AK6 nucleic acids, microRNA, siRNA, shRNA, or activity inhibitors of AK6.

In another preferred embodiment, the inhibitors comprises antibodie(s) of one or more protein(s) selected from Table 1, antisense RNA of the nucleic acid encoding said proteins, microRNA, siRNA, shRNA and the activity inhibitors of the proteins.

In the second aspect of the invention, a use of a male fertility-associated gene or protein or regulatory miRNA thereof or the combination thereof is provided, for preparing (i) a reagent or a kit for detecting male infertility; and/or (ii) a reagent or a kit for estimating the age of a subject who provides the sperm; and/or (iii) a reagent or a kit for estimating the age of human or other mammals, or evaluating the sperm aging and sperm quality.

In another preferred embodiment, the regulatory miRNA comprises regulatory miRNA of AK6, and regulatory miRNA of GPX5.

In another preferred embodiment, the regulatory miRNA of AK6 is selected from the group consisting of miR-370, miR-544a, miR-27a, miR-27b, miR-128, miR-20a, miR-20b, miR-106b, miR-106a, miR-17, miR-200b, miR-200c, miR-93, miR-429, and miR-519d.

In another preferred embodiment, the regulatory miRNA of GPX5 is selected from the group consisting of miR-419-5p, miR-299-3p, miR-296-3p, miR-194, miR-134, miR-383, and miR-206.

In another preferred embodiment, the reagent is a capture reagent of AK6 protein or other male fertility-associated genes or proteins.

In another preferred embodiment, the reagent comprises specific antibody, specific amplimer, probe or chip of AK6 or other male fertility-associated genes or proteins.

In another preferred embodiment, the antibody comprises monoclonal antibody, or polyclonal antibodies, preferably, monoclonal antibody.

In another preferred embodiment, the reagent comprises:
(a) a specific antibody for anti-AK6 protein or other male fertility-associated genes or proteins; and/or
(b) specific primers of mRNA or cDNA for specifically amplifying AK6 or other male fertility-associated genes or proteins.

In another preferred embodiment, the AK6 derives from mammals, preferably, from human or rodent (mice, rat).

In another preferred embodiment, Genebank ID No. of AK6 gene is NM_016283.4.

In another preferred embodiment, the sequence of AK6 protein is set forth in SEQ ID NO.:2, the nucleotide sequence encoding the protein is set forth in SEQ ID NO.: 1.

In another preferred embodiment, the detection comprises qualitative and/or quantitative detection.

In another preferred embodiment, the detection is the qualitative and/or quantitative detection for the sperm localization proteins in the seminal plasma or semen samples from the male individuals.

In another preferred embodiment, detecting subjects of detection are male, preferably, infertile male or the spouse of childless women after 1-year marriage.

In another preferred embodiment, the detection comprises the following detection method: protein chip, antibody chip, DNA chip, RT-PCR, real-time fluorescence quantitative PCR, ELISA, western blotting, immunohistochemistry, immunocytochemistry, flow cytometry, and mass spectrometry.

In the third aspect of the invention, a use of AK6 inhibitors or in combination with the promoters or inhibitors of other male fertility-associated proteins is provided, for preparing (a) a pharmaceutical composition for treating male infertility; and/or (b) anti-aging composition;

wherein said other male fertility-associated proteins comprise one or more proteins listed in Table 1.

In another preferred embodiment, the anti-aging composition comprises a pharmaceutical composition, a cosmetic product composition, or a healthcare product composition.

In another preferred embodiment, the AK6 inhibitors or in combination with the promoters or inhibitors of other male fertility-associated proteins are further used for drug target screening, disease prevention and detection, or evaluation of environmental pollution, health management, genetic analysis, or drug efficacy.

In another preferred embodiment, said other male fertility-associated proteins comprise GPX5 protein.

In another preferred embodiment, the AK6 inhibitors comprise: antibodies of AK6, antisense RNAs of AK6 nucleic acids, microRNA, siRNA, shRNA, and activity inhibitors of AK6.

In another preferred embodiment, the pharmaceutical composition comprise AK6 inhibitors or in combination with other male fertility-associated genes or proteins, or the promoters thereof as active ingredient, and a pharmaceutical acceptable carrier.

In another preferred embodiment, the pharmaceutical composition further comprises the proteins or genes thereof, and the promoters thereof listed in Table 1.

In the forth aspect of the invention, a protein set which affects male fertility and/or success rate of male sperm fertilization is provided, comprising:

(a) AK6 protein, and optional one or more proteins listed in Table 1; or (b) two or more proteins selected from Table 1.

In another preferred embodiment, the protein set comprises CTSB, HSPA5, ALDH4A1, AK6 protein, or combinations thereof.

In the fifth aspect of the invention, a gene set which affects male fertility and/or success rate of male sperm fertilization is provided, the genes in the gene set respectively encode the proteins in the protein set according to the third aspect of the invention.

In another preferred embodiment, the genes comprise the full-length sequences of the genes or fragments, cDNA or mRNA thereof.

In another preferred embodiment, the gene set comprises AK6 gene and GPX5 gene.

In another preferred embodiment, the expression and/or activity of AK6 protein or gene thereof in normal sperm from young males is lower than that in normal sperm from old males.

In another preferred embodiment, the expression and/or activity of the one or more proteins or genes thereof selected from Table 1 in normal sperm from young males is higher than that in normal sperm from old males.

In the sixth aspect of the invention, a kit for detecting male infertility is provided, the kit comprises a container, the container comprises a detecting reagent for detecting the protein set according to the forth aspect of the invention or the gene set according to the fifth aspect of the invention, and label or instructions, and the label or instruction indicates that the kit is used to detect male infertility.

In another preferred embodiment, the detecting reagent comprises the monoclonal antibodies of CTSB, HSPA5, ALDH4A1, AK6 protein, or the combination thereof.

In another preferred embodiment, the male infertility comprises asthenozoospermia, oligozoospermia.

In another preferred embodiment, the label or instructions further includes the following contents:

if the ratio of the expression and/or activity E1 of AK6 gene or protein in the sample from the test subject to the expression and/or the activity E2 of that in normal population, i.e. $E1/E2 \geq 2$; and or if the ratio of the expression and/or activity Ea of one or more genes selected from the group consisting of SEQ ID Nos. 1 to 14 in Table 1 in the sample from the test subject to the expression and/or the activity of that in normal population Eb, i.e. $Ea/Eb \leq 0.5$;

it indicates that the probability of infertility in the test subject is higher than that in general population.

In another preferred embodiment, the sample comprises a blood sample, a urine sample, a seminal plasma/fluid sample, or a tissue sample.

In another preferred embodiment, when the $E1/E2 \geq 2$, and/or $Ea/Eb \leq 0.5$, further indicating that the living environment of a test subject is unsatisfied.

In the seventh aspect of the invention, a chip for detecting the sperm binding protein expressed in testis and epididymis is provided, the chip comprises:

a solid phase support and detection points on the phase support for detecting the protein set according to the forth aspect of the invention.

In another preferred embodiment, the capture reagents (such as antibodies) for the male fertility-associated proteins are fixed at the detective points respectively.

In another preferred embodiment, the capture reagents are the monoclonal antibodies that can specifically bind to the proteins in the protein set according to the third aspect of the invention.

In another preferred embodiment, the protein set at least comprises 1, 2, 3, 4, 5, 6, 7, 8, 9, 10, 11, 12, 13 or 14 proteins shown in Table 1.

In another preferred embodiment, the solid phase support is the support selected from the group consisting of: glass sheets, plastic sheets, nitrocellulose membrane, polyvinylidene fluoride film, microspheres, etc.

In the eighth aspect of the invention, a pharmaceutical composition for improving the success rate of male fertilization is provided; the pharmaceutical composition comprises (a) AK6 inhibitors; optionally (b) one or more proteins or genes or promoters thereof selected from Table 1; and (c) a pharmaceutically acceptable carrier.

In another preferred embodiment, the inhibitors comprise a monoclonal antibody for AK6 protein.

In the ninth aspect of the invention, a contraceptive pharmaceutical composition is provided, the pharmaceutical composition comprises (a1) AK6 gene or protein; optionally (b1) one or more antagonists of the proteins or genes listed in Table 1; and (c1) a pharmaceutically acceptable carrier.

In the tenth aspect of the invention, a method for detecting or diagnosing male infertility is provided, comprising the following steps:

(i) detecting the expression and/or activity of the protein set according to the forth aspect of the invention or the gene set according to the fifth aspect of the invention in the sample from a subject;

(ii) detecting or diagnosing whether the subject is suffering from male infertility according to the determination results of (i);

if the ratio of the expression and/or activity E1 of AK6 gene or protein in the sample from the test subject to the expression and/or the activity E2 of that in normal population, i.e. E1/E2≥2; and or if the ratio of the expression and/or activity Ea of one or more genes selected from the group consisting of SEQ ID Nos. 1 to 14 in Table 1 in the sample from the test subject to the expression and/or the activity of that in normal population Eb, i.e. Ea/Eb≤0.5;

it indicates that the probability of infertility in the test subject is higher than that in general population.

In another preferred embodiment, the method for detecting further comprises the detection for AK6 regulatory miRNA.

In another preferred embodiment, the AK6 regulatory miRNA comprises: miR-370, miR-544a, miR-27a, miR-27b, miR-128, miR-20a, miR-20b, miR-106b, miR-106a, miR-17, miR-200b, miR-200c, miR-93, miR-429, or miR-519d.

In another preferred embodiment, comparing with the sperms in normal population, the expressions of miR-370, miR-544a, miR-27a, miR-27b, miR-128, miR-20a, miR-20b, miR-106b, miR-106a, miR-17, miR-200b, and miR-200c are decreased in patients with oligospermia.

In another preferred embodiment, comparing with the sperms in normal population, the expressions of miR-93 and miR-429 are decreased in patients with oligospermia.

In another preferred embodiment, comparing with the sperms in normal population, the expression of miR-519d is significantly decreased in the old, and patients with asthenozoospermia and oligospermia.

In another preferred embodiment, the AK6 regulatory miRNA is lowly expressed in the test subject, indicating that the probability of infertility in the test subject is higher than that in normal population.

In another preferred embodiment, the method for detecting further comprises the detection for GPX5 regulatory miRNA.

In another preferred embodiment, GPX5 regulatory miRNA comprises:

miR-419-5p, miR-299-3p, miR-296-3p, miR-194, miR-134, miR-383, or miR-206.

In another preferred embodiment, the GPX5 regulatory miRNA is highly expressed in the test subject, indicating that the probability of infertility in the test subject is higher than that in normal population.

In the eleventh aspect of the invention, a method for improving the success rate of male fertilization and/or treating infertility is provided, comprising: contacting a sperm capacitation liquid with a pharmaceutical composition according to the ninth aspect of the present invention, or one or more of substances selected from the group consisting of:

(a1) AK6 inhibitors;
(b1) one or more proteins or genes or promoters thereof selected from Table 1;
combination of (a1) and (b1);
thereby improving the success rate of male fertilization and/or treating male infertility.

In the twelfth aspect of the invention, a method for estimating the age of a subject for providing the sperm; and/or determining sperm cell aging; and/or evaluating the quality of sperm and cell is provided, comprising the steps of: (i) detecting the expression and/or activity of the protein set according to the forth aspect of the present invention or the gene set according to the fifth aspect of the present invention in the sample from a test subject;

(ii) determining the age range, or the aging of the sperm cells, or the quality of sperms and cells of the subject based on the determination results of (i).

In another preferred embodiment, if AK6 protein is highly expressed in sperms (sperm cells), and one or more proteins selected from Table 1 are low expressed in sperms (sperm cells), it indicates that the subject who provides the sperm is older, the cell aging degree is higher, or the sperm quality is poorer.

In another preferred embodiment, if AK6 protein is lowly expressed in sperms (sperm cells), and one or more proteins selected from Table 1 are highly expressed in sperms (sperm cells), it indicates that the subject who provides the sperm is younger, the cell aging degree is lower, or the sperm quality is better.

It should be understood that in the present invention, any of the technical features specifically described above and below (such as in the Examples) can be combined with each other, thereby constituting new or preferred technical solutions that are not described one by one in the specification.

DETAILED DESCRIPTION OF INVENTION

Figure 1:
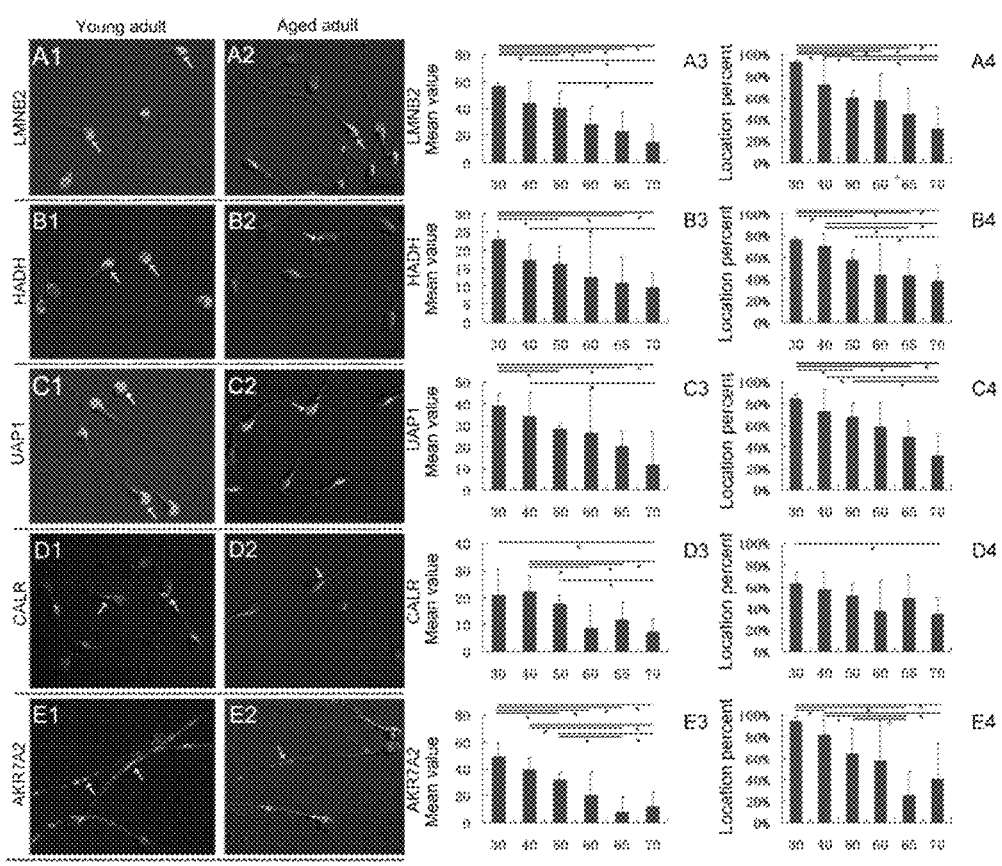
FIG. 1 shows an immunofluorescent localization of sperm localization proteins LMNB2, HADH, UAP1, CALR, AKR7A2, GPX5, HSPA5, and CTSB in the sperms from young people (30±2 years) and the aged (70±2 years) (FIG. 1, A1-I1, FIG. 1, A2-I2), and their statistical analysis results of quantitation (FIG. 1, A3-I3) and localization rate (FIG. 1, A4-I4) on sperms in 6 different age groups of 30, 40, 50, 60, 65, 70 (±2) years. Wherein the bar represents 20 μm, red ethidium bromide stain indicates the nucleus, white arrow indicates the localization of target proteins stained with green fluorescein isothiocyanate on the sperm.

Upon comprehensive and intensive studies, the inventors discovered a close relationship between adenosine kinase 6 (AK6) protein and male infertility, that is, the expression level of AK6 and activity are increased in male infertility patients, and the expression level of AK6 and activity are also increased with age in normal population. Based on the experiment, the inventors further discovered that decreasing the expression level of AK6 and/or activity can enhance the success rate of male fertilization. In addition, the inventors further discovered that the combination of AK6 and 14 proteins in Table 1 is helpful for diagnosing male infertility. There will be therapeutic effects on male infertility, in particular, asthenozoospermia and oligo asthenozoospermia when decreasing the expression level and/or activity of AK6, or simultaneously increasing the expression level and/or activity of one or more proteins selected from 14 proteins in Table 1. Based on the above findings, the present invention is completed.

Sperm Localization Proteins

As used herein, the term "the protein of the present invention", "male fertility-associated proteins", "sperm localization proteins of the present invention", "sperm localization proteins" and "age-related sperm localization proteins" can be used interchangeably, referring to the protein that is age-related and localized in sperms, and can be expressed in the testis and/or epididymis of male mammals (especially, humans). The relevant molecular biological materials include, but are not limited to, mutant proteins, any fragment of proteins, genes and any DNA fragment, mutant genes, mRNA, interfering RNA, antibodies thereof and the like. Representative sperm localization proteins include 14 down-regulated proteins and one up-regulated protein (AK6) shown in Table 1.

As used herein, the term "mammals" refer to a mammalian species that is viviparous and the offspring are breast-fed a representative mammal belonging to vertebrates includes (but not limited to), for example, human, monkey sheep cow, rabbit, horse, mouse, rat and the like, in particular, human is preferred.

Among the 14 proteins shown in Table 1, the contents of 14 proteins are low in the sperms of the old and the asthenozoospermia, classified as the down-regulating sperm localization proteins (SEQ ID NO.: 1-14) expressed in the old or the asthenozoospermia; the contents of another protein of the present invention (AK6) are high in the sperms of the old and the asthenozoospermia, classified as the up-regulating sperm localization protein expressed in the old or the asthenozoospermia.

TABLE 1

15 age-related human sperm localization proteins

| No. | Lab NO. | SEQ ID NO.: | gene name | Access Numbers of the reference sequence | Access Numbers of the present invention | sperm localization |
|---|---|---|---|---|---|---|
| 1 | HEL-S-9a | 4 | LMNB2 | NM_032737.2 | GQ891286 | acrosome |
| 2 | HTL-S-203a | 6 | HADH | NM_005327.4 | HM005616 | acrosome |
| 3 | HTL-T-37a | 8 | UAP1 | NM_003115.4 | HM005660 | acrosome |
| 4 | HEL-S-99n | 10 | CALR | NM_004343.3 | FJ224311 | neck |
| 5 | HEL-S-166mP | 12 | AKR7A2 | NM_003689.3 | EU794591 | middle section and main section of tail |
| 6 | HEL-S-158am | 14 | CTSB | NM_001908.3 | GQ891351 | acrosome and middle section of tail |
| 7 | HEL-S-89n | 16 | HSPA5 | NM_005347.4 | EU794617 | neck |
| 8 | HEL-S-75p | 18 | GPX5 | NM_001509.2 | FJ460514 | post-acrosome |
| 9 | HEL-S-35a | 20 | KLHL15 | NM_030624.2 | GQ891312 | acrosome |
| 10 | HEL-S-109n | 22 | HSPA1L | NM_005527.3 | GQ891337 | neck |
| 11 | HEL-S-135P | 24 | GP83 | NM_003817.3 | GQ891358 | main section of tail |
| 12 | HEL-S-127m | 26 | CLDN7 | NM_001307.4 | GQ891357 | middle section of tail |
| 13 | HEL-S-174mP | 28 | ALDH4A1 | NM_003748.2 | GQ891378 | main and middle section of tail |

TABLE 1-continued 15 age-related human sperm localization proteins

| No. | Lab NO. | SEQ ID NO.: | gene name | Access Numbers of the reference sequence | Access Numbers of the present invention | sperm localization |
|---|---|---|---|---|---|---|
| 14 | HEL-S-143P | 30 | ALDH2 | NM_000690.2 | GQ891366 | main section of tail |

The nucleotide sequences encoding the proteins as set forth by SEQ ID NO.: 4, 6, 8, 10, 12, 14, 16, 18, 20, 22, 24, 26, 28, and 30 are respectively set forth by SEQ ID NO.: 3, 5, 7, 9, 11, 13, 15, 17, 19, 21, 23, 25, 27, and 29.

Protein Set

A protein set for diagnosing or treating male infertility is provided by the present invention, the protein set at least comprises AK6 and other male infertility-associated proteins, especially sperm localization proteins. Generally, as used herein, the term "other male infertility-associated proteins" refers to proteins found in the prior art that are associated with male infertility. Preferably, the protein set of the present invention comprise AK6 and one or more sperm localization proteins selected from Table 1. Wherein, AK6 protein in the present invention is a newly discovered protein which is closely related with male infertility and differentially expressed in the young people and the aged.

It should be understood that the protein set of the present invention comprise (a) AK6 protein, and optionally one or more proteins selected from Table 1; or (b) any 2, 3, 4, 5, 6, 7, 8, 9, 10, 11, 12, 13 or 14 of proteins selected from Table 1.

Upon experiments, the inventors have found that the expression level and/or activity of AK6, any proteins selected from Table 1 or a combination thereof is significantly different between the sperms from the young people and the aged, so that it can be used as target proteins for determining sperm aging and hypofunction. Upon intensive studies, the inventors have further discovered the differential expression of some of these proteins between the patients who have already been diagnosed as asthenozoospermia and oligo asthenozoospermia and the normal populations (the young people).

Based on the above experimental results, the protein set used for diagnosing or treating male infertility are obtained by the inventors. That is, it is helpful to determine or predict the probability of infertility in the test subject by combining Ak6 with proteins in the prior art (in particular, Table 1 of the present invention) to form the protein set and determining the expression level and/or activity of these protein set. Developing the antibodies against these protein set contributes to the treatment of male infertility or the development of contraceptive drugs. For example, for preparing monoclonal antibodies to AK6 proteins.

It should be understood that the protein set of the present invention can be a set formed by Ak6 and any male infertility-associated proteins. By regulating the expression level and/or activity of Ak6 or other male infertility-associated proteins, pharmaceutical compositions for improving fertilization rate (promoting fertility) or decreasing fertilization rate (contraception) can be prepared respectively.

In addition, a gene set for encoding the protein set of the present invention is provided, comprising cDNA, a complete gene sequence for encoding the proteins, or the nucleic acids having an identity of ≥70%, ≥80%, more preferably, ≥85%, ≥90%, ≥95%, comparing with the original encoded. By using the gene (or encoding nucleic acid) set, the antisense nucleic acids thereof can be prepared by the conventional means, or the mRNA thereof can be determined, or these genes can be qualitatively or quantitatively detected by detecting the corresponding miRNA.

miRNA

A target gene set for diagnosing or predicting/detecting infertility is provided, the expression level of the gene sets can be determined by using known miRNA of each gene in the gene sets of the present invention.

A preferred gene regulatory-associated miRNA is shown below:

Among the AK6 gene regulatory-associated miRNAs, the expressions of miR-370, miR-544a, miR-27a, miR-27b, miR-128, miR-20a, miR-20b, miR-106b, miR-106a, miR-17, miR-200b, and miR-200c are decreased in the oligo asthenozoospermia group, the expressions of miR-93, miR-429 is decreased in the asthenozoospermia group, and the expression of miR-519d is significantly decreased in the aged, the asthenozoospermia and the oligo asthenozoospermia group. The sequences of AK6 gene regulatory-associated miRNAs are shown below:

| miRNA | SEQ ID NO | Sequence |
|---|---|---|
| hsa-miR-128 | 31 | TCACAGTGAACCGGTCTCTTT |
| hsa-miR-27a | 32 | TTCACAGTGGCTAAGTTCCGC |
| hsa-miR-27b | 33 | TTCACAGTGGCTAAGTTCTGC |
| hsa-miR-200b | 34 | TAATACTGCCTGGTAATGATGA |
| hsa-miR-200c | 35 | TAATACTGCCGGGTAATGATGGA |
| hsa-miR-429 | 36 | TAATACTGTCTGGTAAAACCGT |
| hsa-miR-370 | 37 | GCCTGCTGGGGTGGAACCTGGT |
| hsa-miR-544a | 38 | ATTCTGCATTTTTAGCAAGTTC |
| hsa-miR-106b | 39 | TAAAGTGCTGACAGTGCAGAT |
| hsa-miR-519d | 40 | CAAAGTGCCTCCCTTTAGAGTG |
| hsa-miR-106a | 41 | AAAAGTGCTTACAGTGCAGGTAG |
| hsa-miR-17 | 42 | CAAAGTGCTTACAGTGCAGGTAG |
| hsa-miR-20a | 43 | TAAAGTGCTTATAGTGCAGGTAG |
| hsa-miR-20b | 44 | CAAAGTGCTCATAGTGCAGGTAG |
| hsa-miR-93 | 45 | CAAAGTGCTGTTCGTGCAGGTAG |

While among the GPX5 gene regulatory-associated miRNAs, the expressions of miR-419-5p, miR-299-3p, miR- 296-3p, miR-194, miR-134, miR-383, miR-206 are significantly increased in the patients with asthenozoospermia and oligo asthenozoospermia. The sequences of GPX5 gene regulatory-associated miRNAs are shown below:

| miRNA | SEQ ID NO.: | Sequence |
| --- | --- | --- |
| hsa-miR-194 | 46 | TGTAACAGCAACTCCATGTGGA |
| hsa-miR-134 | 47 | TGTGACTGGTTGACCAGAGGGG |
| hsa-miR-206 | 48 | TGGAATGTAAGGAAGTGTGTGG |
| hsa-miR-383 | 49 | AGATCAGAAGGTGATTGTGGCT |
| hsa-miR-296-3p | 50 | GAGGGTTGGGTGGAGGCTCTCC |
| hsa-miR-299-3p | 51 | TATGTGGGATGGTAAACCGCTT |
| hsa-miR-491-5p | 52 | AGTGGGGAACCCTTCCATGAGG |

Therefore, the skilled person in the art can determine every gene regulatory-associated miRNAs in the genomes of the present invention based on the teaching of the present invention and the miRNA-screening methods in the prior art, thereby developing more detection reagents or kits related with male infertility, and pharmaceutical compositions for treating male infertility.

Detection Method

In the present invention, a method for qualitatively or quantitatively detecting 15 sperm localization proteins of the present invention and the related molecular biological materials thereof is provided, wherein including (but not limited to): detection for human sperm localization proteins, gene mutation, mRNAs for gene transcription, regulatory-associated miRNA, mutein, and protein activity. The biological samples for the detection include (but are not limited to): sperm, semen, urine, blood, or prostatic fluid.

Representative detection method includes (but not limited to): protein chip, antibody chip, DNA chip, liquid chip, ELISA, immunoblotting, RT-PCR, real time fluorescence quantitative PCR, immunohistochemistry, immunofluorescence, flow cytometry, mass spectrometry, capillary electrophoresis, immunoprecipitation, enzyme activity assay, and the like.

Asthenozoospermia

According to the fifth edition of the WHO Human Semen Laboratory Test Manual, it is deemed as asthenozoospermia when the percentage of progressive (PR) sperms is less than 32%. The asthenozoospermia of the present invention refers to the asthenozoospermia in young people with other indexes (such as teratospermia rate, sperm density, white blood cell numbers, semen volume, and the like) in semen routine substantially normal.

Oligo Asthenozoospermia

The term "oligo asthenozoospermia" of the present invention refers to those people having a progressive sperm percentage<32% in semen, a sperm concentration less than $15 \times 10^6$/ml or the sperm amounts for one ejaculation<$39 \times 10^6$.

Qualitative or Quantitative Detection for Sperm Localization Proteins on Human Sperm The qualitative or quantitative method for detecting human sperm localization proteins of the present invention is not specifically limited. It can be any instruments, software or means in the art for detecting fluorescence intensity or fluorescence value.

Generally, after the incubation of the specific antibodies with the test sample (sperm), the localization of the sperm localization proteins are determined by fluorescent labeled second antibodies, thereby calculating the localization rate and contents of the proteins by the scanning results through Laser Scanning Confocal Microscope. The method for quantifying the sperm protein expression by Laser Scanning Confocal Microscope is shown below: an immunofluorescence slide is observed at a magnification 400×. The view containing sperms are observed sequentially (the view is required for the condition of no non-sperm cells, no overlap on the tail of the sperms, the tail of the sperms should be intact in the view) until the total number of the sperms in the view reaches 200. Background Fluorescence was measured in a blank area without sperms. Sperms with fluorescence values below or above the blank value (the mean value is approximately 10) were used for statistics of stained sperms ratio. LSM 510 META software (LSM 5 version 3.2) automatically measures the fluorescence values of all stained sperms, removes the fluorescence background threshold, and then obtains the mean immunofluorescence intensity values of the stained sperms. The detection results of this method are consistent with that obtained by flow cytometry. The detection method for the localization rate and contents of the proteins by flow cytometry is shown below: sperm washing and preparation is treated as the former, the fluorescence values of the sperm samples are determined by BD flow cytometry, counting 10,000 sperms, and the stained cell ratio and stained cell fluorescence intensity are analyzed by Cellquest software.

The specific antibodies labeled with fluorescence can be dissolved in a solution and bind to the sperm surface, and the expression levels of the sperm surface proteins can be detected qualitatively or quantitatively by the detecting means such as flow cytometry; alternatively, the antibodies can be fixed on the supports (e.g., polyethylene plates, immune microspheres, glass slides, nitrocellulose (NC) membrane and PVDF film, etc.), and the percentage of the positive sperm can be detected qualitatively or quantitatively with an ordinary scanner; further, the antibodies can be coupled to the magnetic beads or plastic beads, and the sperm localization proteins in the samples such as semen or sperm lysate can be detected qualitatively or quantitatively by a dual-antibody sandwich assay through a liquid chip.

Protein Chip and the Use Thereof for Sample Detection Such as Human Seminal Plasma The present invention also provides protein chips used for detecting sperm localization proteins. The chips can be used to qualitatively or quantitatively detect the content of sperm localization proteins in a test sample. The detection results can be used to aid the determination of sperm quality, functional level of the sperms and/or the cause for the decrease of sperm quality.

The term "protein arrays" or "protein chips" can be used interchangeably and both refer to the arrays of capture reagents which can bind to the protein markers. Typically, the capture reagents can be polyclonal or monoclonal antibodies which can bind to the specific proteins. After the markers are captured and then detected by the labeled detectable molecules, thereby achieving the goals for the qualitatively or quantitatively (using the standards) detection.

The protein chips of the invention are characterized in that the detection points for sperm localization proteins are set on the chips. As used herein, the term "detection point" refers to the spotting point used for detecting the corresponding protein on a protein chip. For example, the detection point used for detecting Protein AK6 is generally formed by spotting the monoclonal antibody of anti-AK6 protein on chip substrates or coupled to the magnetic beads or plastic beads.

The protein chips suitable for the present invention are not particularly limited. Any blank protein chips with known structures in the art can be used. Generally, supports for these protein chips include: immune microspheres, glass sheets, plastic sheets, nitrocellulose (NC) film, and PVDF film, in which the immune microspheres and various substrates are particularly preferred. The purpose for detecting various proteins can be achieved by orderly fixing peptides, proteins or antibodies on various supports through the methods such as in-situ synthesis, mechanical spotting or covalent binding to form the chip for detection, fluorescence-marked antibodies or other components interacting with the chip, washing off the components which fail to bind to the complementary proteins on the chip by rinsing, and then using a fluorescence scanner or a confocal laser scanning technology to detect the fluorescence intensity of each point on the chip or other supports and the strength of markers for analyzing the content of each protein, thereby achieving the goals for the determination of each protein.

Protein chip of the invention may comprise detection points for one or more sperm localization proteins shown in Table 1, for example, 1, 2, 3, 4, 5, 6, 7, 8, 9, 10, 11, 12, 13, 14 or 15 sperm localization proteins disclosed for the first time in the invention. These 15 detection points can be used alone or in any combinations, or used in combination with sperms detection index in the prior art for evaluating the sperm quality or diagnosing male infertility, etc.

INDUSTRIAL APPLICATIONS

Sperm production, maturation and aging are mainly reflected by the amount of protein molecules secreted by testicular epididymal and binded on the sperm. The increase, reduction or impairment of sperms will lead to dysmaturity or dysfunction, resulting in male infertility. Based on the present invention, the detection method and the detection means for sperm localization proteins can be used to detect the content of 15 age-related sperm localization proteins, thereby determining the sperm quality and diagnosing male infertility.

For example, some detecting or diagnosing results, such as sperm quality, sperm healthy status, infertility or not, etc., are obtained by measuring the content of 14 down-regulated sperm localization proteins. In a word, high contents of the 14 sperm localization proteins indicates a good health condition, a good quality of the sperms or the sperms are from the normal young; low contents of the 14 sperm localization proteins indicates a poor health condition of the sperm or the sperms are from the aged.

In addition, it is helpful for improving the healthy condition of the sperms and enhancing the sperm activity by supplementing one or more proteins selected from 14 down-regulated sperm localization proteins.

For the normal population, it will be helpful for contraception by reducing the expression or activity of 14 down-regulated sperm localization proteins through antibody blocking or siRNA interference, etc.

As for different fields, the representative applications include (but not limited to):

(a) The evaluation of the sperm quality and health condition: the sperm health condition and quality are evaluated by determining the content of the proteins of the present invention on the sperm or in the seminal plasma. The content of 14 down-regulated proteins is low or zero, the content of one up-regulated protein (such as protein AK6) is high, indicating a poor sperm health condition, low sperm quality and sperm impairment; otherwise, indicating a good sperm health condition and high sperm quality.

(b) The diagnosis for male infertility: the male infertility is diagnosed by determining the content of the protein of the present invention on the sperm or in the seminal plasma. The content of 14 down-regulated proteins is low or zero, the content of one up-regulated protein is high, indicating the possible occurrence of infertility.

(c) The evaluation for the environmental pollution: a preventive detection for reproductive health or an environmental pollution evaluation is performed by determining the protein contents of the present invention on the sperm. For those living in different places, the lower the protein content is, the worse the living environment is. It is helpful to estimate the environment-related problems by statistical analysis on a large number of people.

(d) Management of human health: determining the protein contents of the present invention in human samples (such as blood, urine, seminal plasma, tissue, etc.). A result beyond normal range indicates a possible health problem, which needs a further inspection or diagnosis.

(e) Age identification: for example, in the field of forensic medicine, age can be identified or assisted determined by determining the protein contents of the present invention.

(f) Healthcare and therapeutic application: By supplementing the protein of the present invention, diseases related to the function of the protein can be treated, and the sperm motility can be enhanced and the male infertility can be treated. For example, a suppository can be prepared and non-invasively used for female reproductive tract; or an injection can be prepared for male (local injection, subcutaneous injection, etc.).

(g) Contraception: preparations (such as suppositories) can be made for contraception by using the antibodies against the protein of the present invention.

(h) Drug target and Screening: the protein of the present invention can be used as a drug target for screening contraceptive drugs or therapeutic drugs for male infertility.

(i) Evaluation of therapeutic effect: The content variation of the protein of the present invention can be used as an auxiliary index for evaluating the curative effect on treating male infertility.

(j) Toxicity test: the effect of drugs, chemicals, cosmetics, etc. on reproduction can be evaluated by determining the content variation of the protein in animal sperms or seminal plasma.

The above applications can be achieved not only by determining content viaration of 15 proteins in human samples, but also by detecting gene mutations, transcription levels, amino acid changes, addition or deletion of the nucleotides or amino acids, regulatory-associated miRNA level, antibodies, and the like.

The main advantages of the invention mainly include:

(a) A detection result of contents of age-related sperm localization proteins can be rapidly and effectively obtained.

(b) The protein-related molecule biological materials and the detection methods thereof of the present invention contribute to the promotion of the diagnosis, treatment, or prevention—related medical technologies for male infertility and the development of diagnostic agents, therapeutic agents, prophylactic drugs or contraceptives.

(c) The protein of the present invention can also be used to determine the age of human or other mammals, or evaluate the cells aging and sperm and cell quality, or develop anti-aging products.

The present invention will be further illustrated below with reference to specific examples. It should be understood that these examples are only to illustrate the present invention but not to limit the scope of the present invention. The experimental methods with no specific conditions described in the following examples are generally performed under conventional conditions, such as the conditions described in Sambrook et al, molecular cloning: the Laboratory manual (New York: Cold Spring Harbor Laboratory Press, 1989), or according to the manufacture's instruction.

General Method

Gene Cloning, Prokaryotic Expression and Protein Purification

The protein product of the above-mentioned 15 genes can be obtained by the following method. Based on the gene sequence, a pair of specific primers for amplifying the mature coding region was synthesized. Human epididymal cDNA library prepared by the conventional method was used as a template, the target gene was directly amplified by PCR, and then cloned into a commercially available vector pGM-T vector (available from Shanghai Beibo Biotech Co., Ltd.) for sequencing and identification. The sequenced and identified genes were cloned into the expression vector pET32b(+) (available from Shanghai Beibo Biotech Co., Ltd.) by restriction enzyme sites, rendering it consistent with the reading frame of the fusion tag. The recombinant expression vector was transformed into E. coli BL21(DE3), induced expression by IPTG, the thallus was ultrasonic fragmented, the recombinant protein was separated and purified according to the His-tag of the vector by "two-step nickel affinity chromatography".

Example 1 Quantitative Analysis of 15 Sperm Localization Proteins in Table 1 on Human Sperms of Different Ages 30 semen samples (30, 40, 50, 60, 65, 70±2 years old) of normal populations with different ages were respectively collected, all without the record of reproductive system diseases. After the semen was completely liquefied, 1 ml semen was added into a 15 ml sterile conical bottom tube, and then PBS was added to 8 ml, respectively, and the mixture was gently blown and mixed and centrifuged at 500 g for 15 min. The supernatant was discarded, and then washed twice with PBS (500 g, 10 min), the supernatant was discarded. The collected sperm precipitation was adjusted to a sperm concentration of $1\times10^6$ cells/ml with PBS containing 3% (w/v) BSA, and plated on the slides coated with 0.1% gelatin, dried at the room temperature, fixed with methanol for 10 min at −20° C., washed three times with PBS for 5 min after drying; and then a primary antibody against the target protein was dropwise added (diluted with PBS containing 3% BSA as 1:50), and incubated at the room temperature for 1h. PBS was used for washing for 3 times, 5 min for each. A second antibody labeled with FITC (diluted with PBS containing 3% BSA as 1:100) was added and subjected to incubation in room temperature for 1 h. PBS was used for washing for 3 times, 5 min for each. Counterstain was conducted with PI. The product was washed twice with distilled water, 10 min for each, sealed with buffer glycerol, and respectively subjected to Meta 510 laser confocal microscope (Zeiss, Germany) for protein localization and quantification analysis.

Figure 2:
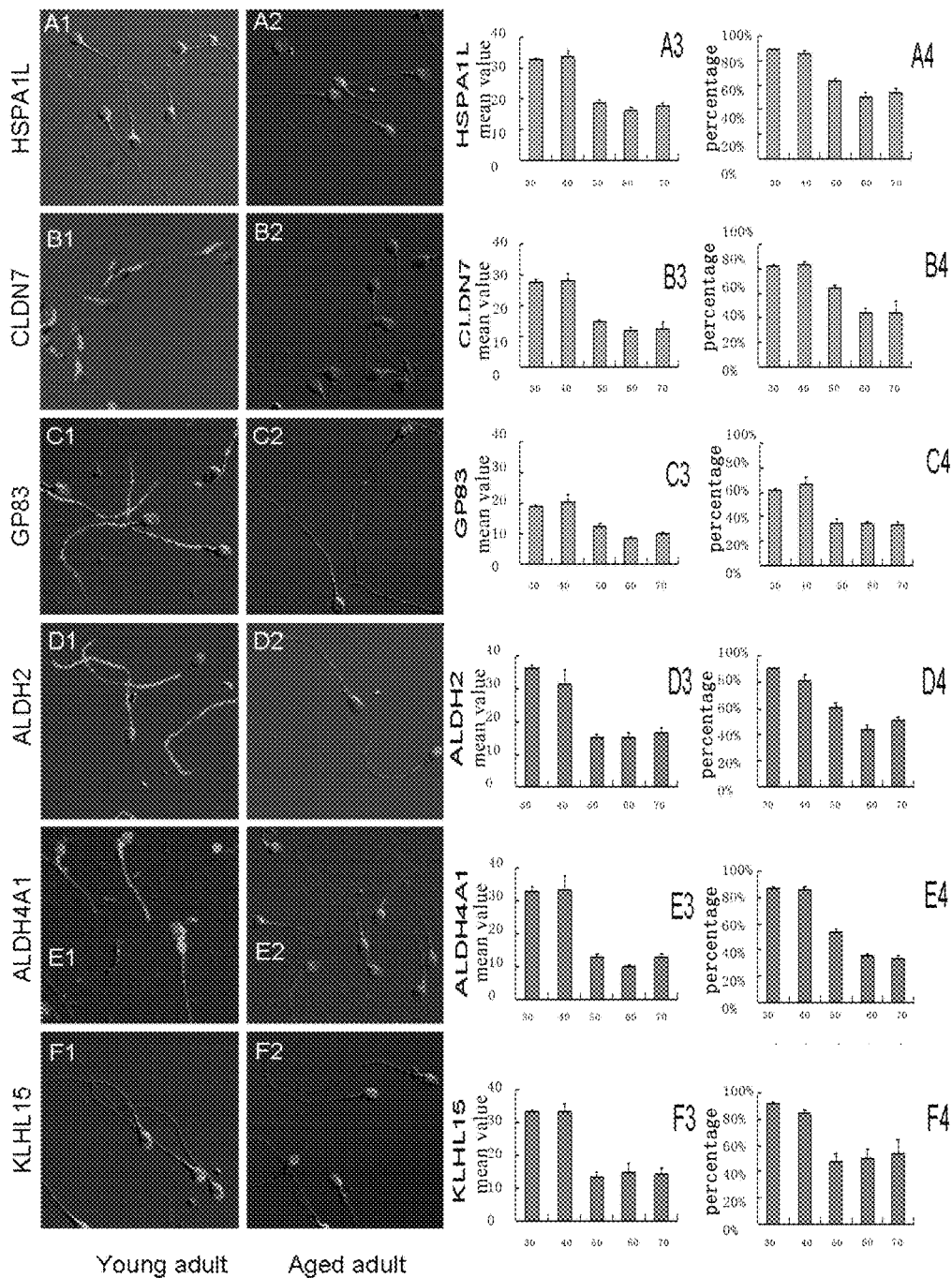
FIG. 2 shows an immunofluorescent localization of sperm localization proteins HSPA1L, CLDN7, GP83, ALDH2, ALDH4A1, and KLHL15 in the sperms from young people (30±2 years) and the aged (70±2 years) (FIG. 2, A1-F1, FIG. 2, A2-F2), and their statistical analysis results of quantitation (FIG. 2, A3-F3) and localization rate (FIG. 2, A4-F4) on sperms in 5 different age groups of 30, 40, 50, 60, 70 (±2) years. Wherein the bar represents 10 μm, red ethidium bromide stain indicates the nucleus.

Results are shown in FIG. 1 and FIG. 2, the localization rate and contents of 14 sperm localization proteins (14 proteins, 1-14, Table 1) on sperms show a gradual decrease trend with age-increasing. Localization proteins deletion phenomenon was found in some sperms from the old.

However, sperm localization protein Ak6 of No. 15 in Table 1 is upregulated, and the localization rate and contents of which on sperms from the old are significantly higher than that from the young people (see FIG. 4, FIG. 5), indicating that high expression of AK6 protein in the sperms from the old may be is a compensation for alleviating the low energy state of the sperms.

Figure 3:
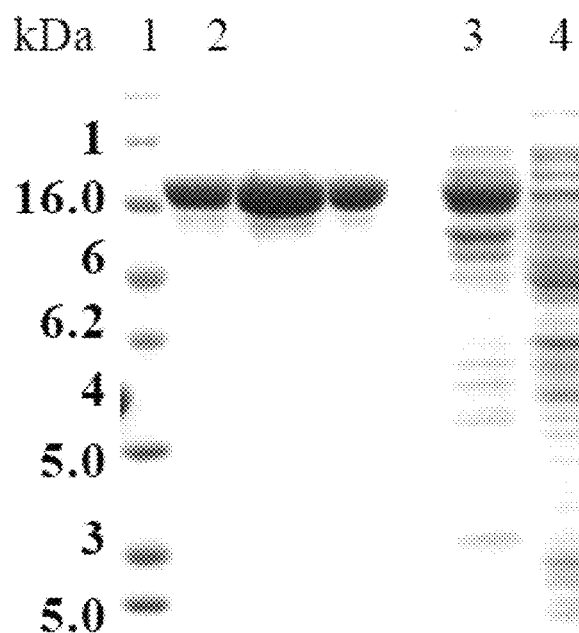
FIG. 3 shows the SDS-PAGE electrophoresis of the sperm localization protein HSPA5 upon expression and purification. Wherein each lane is shown as follows: 1. Marker; 2. HSPA5 protein (also referred as GRP78 protein) upon affinity purification; 3. lysate supernatant; 4. the removed impure proteins during affinity-purification.

Example 2 Identification of Recombinant Proteins 15 purified recombinant proteins were quantitative identified by Bradford method (Bradford 1976), and then freeze-dried for storage. FIG. 3 shows an expression and purification SDS-PAGE result for one of 15 sperm localization proteins, that is, a protein corresponding to HSPA5 gene (also known as GRP78 protein).

The purified recombinant protein is identified as the protein of the present invention.

Figure 4:
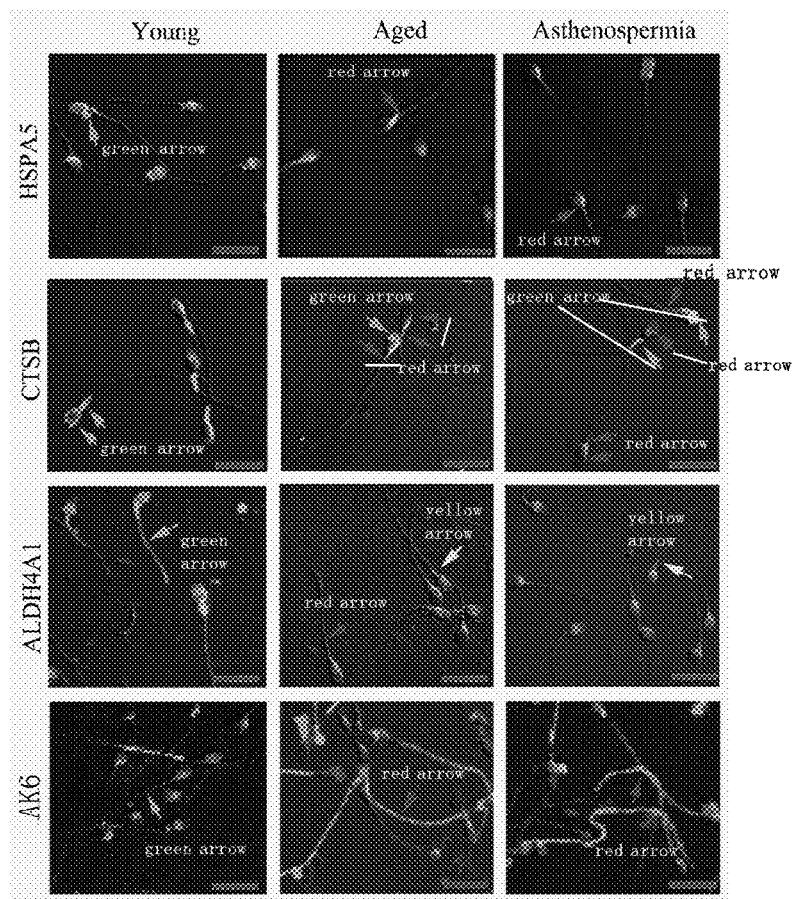
FIG. 4 shows a fluorescence localization and intensity of CTSB, HSPA5, ALDH4A1, and AK6 on the sperm of young people (30±2 years), the aged (70±2 years) and Asthenozoospermia. Green arrows refers to the phenotype of the sperm localization proteins from normal young people, yellow arrows refers to phenotype of the sperm localization proteins with decreased expression in young people suffering asthenozoospermia, red arrows refers to the enhanced or deleted phenotype of the sperm localization proteins, with a scale of 10 μm.
Figure 5:
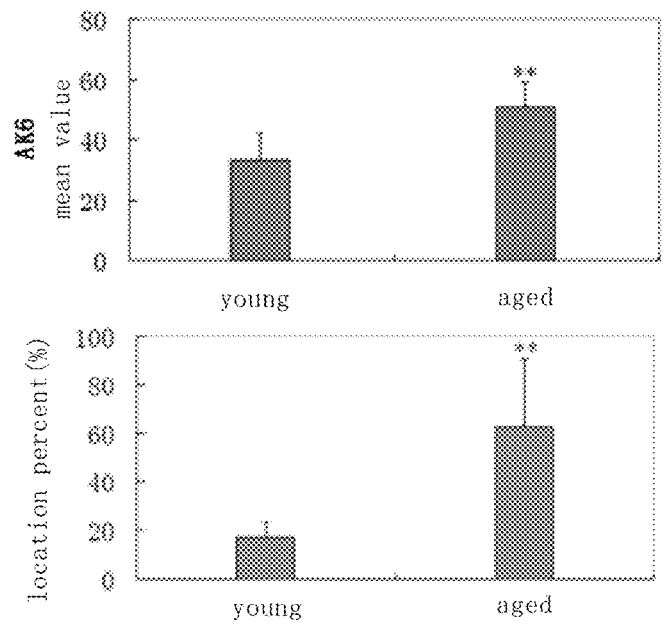
FIG. 5 shows a statistical analysis result of AK6 quantitation and localization rate on the sperms from young people (30±2 years) and the aged (70±2 years).

Example 3 Analysis of Sperm-Associated Proteins in Asthenozoospermia 102 cases of young asthenozoospermia samples were collected, the localization rate and contents of CTSB, HSPA5, ALDH4A1 and AK6 on sperms with asthenozoospermia were quantitatively analyzed. The specific method is the same as that in Example 1, the results are shown in FIG. 4.

The results show that the percentage of significant lost of those three proteins, ie, CTSB, HSPA5 and ALDH4A1 is 45.1%, 45.1% and 57.8%, respectively, with a total coverage rate reaching 85.5%. That is, over 85% sperms with asthenozoospermia have expression defection in at least one of the above-mentioned proteins, while AK6 shows an increasing trend. It can be seen that it is helpful to diagnose asthenozoospermia and male infertility by quantitatively detecting the 4 proteins on sperms.

Example 4 Preparation and Application for Monoclonal Antibodies 4.1 Preparation for Monoclonal Antibodies The monoclonal antibodies against the proteins of the present invention can be obtained by the conventional preparation method; preferably, the present example can be obtained by the following method: each purified recombinant protein of the present invention was used to immunize BALB/C mice respectively. Each mouse was injected on the first day with 50 μg of recombinant protein and the same amount of Complete Freund's Adjuvant (CFA). Then, 25 μg of recombinant protein and the same amount of Incomplete Freund's Adjuvant (IFA) were injected on the 15th, 30th and 45th days for booster immunization. 3 to 4 days after the last immunization, spleen cells were separated and mixed with Sp2 myeloma cell strains and PEG was added for cell fusion, the fused cells were diluted properly and placed into well plate respectively for culture. Generally, they were diluted to 0.8 cells/well. When the cells had been cultured to cover 20% of the well bottom, the supernatant was drawed and detected for the content of antibodies by ELISA. Screened positive cells were inoculated intraperitoneally into mice, and the ascites was collected. The antibodies were riched to the affinity column which was prepared by staphylococcal protein A and eluted, thereby recovering the monoclonal antibodies.

4.2 Immunofluorescence Localization of the Proteins Using Monoclonal Antibodies of 4.1

Sperms were collected, washed with PBS, and then smeared on the slides coated with 1% gelatin, naturally dried and fixed for 10 minutes with methanol. Slides with sperms were blocked for 1 hour with 3% BSA at room temperature, and then each monoclonal antibodies obtained by 4.1 were added (1:200) and kept overnight at 4° C. The product was washed for three times with PBST (PBS containing 0.1% Tween-20), and the corresponding secondary antibodies (1:200) of FITC-labeled goat anti-mouse IgG were added. The slides were washed for three times with PBST, and 80% glycerol was used for blocking. Olympus BX-52 microscope was used to observe the results. The results are shown in Table 1. Proteins located at the tail, neck and acrosome and other parts of the mature sperm respectively.

Example 5 Preparation for the Protein Chips

Protein chips No. 1-3 were prepared by the following method:

a Slide Chip No. 1

(1) a high-speed spotting instrument was used for directly and intensively spotting the protein samples (antibodies against the proteins of the present invention) in the multi-well plate on the slides which have been chemically treated and have activated aldehyde groups on the surface. There are 15 sample spots (corresponding to 15 proteins No. 1-15 of Table 1 respectively) for each array, and the diameter of each sample spot is 0.4 mm;

(2) incubating the slides at room temperature overnight or at 37° C. for 1 hour for fixing the sample through the condensation reaction between the amino groups on the protein and the aldehyde groups on the slide;

(3) activated aldehyde groups not occupied by the proteins on slides were reduced and the slides were washed thoroughly and dried at room temperature;

(4) finally, the slides were sealed with photophobic materials and stored under 4° C.

b PDVF Film Chip No. 2

(1) a high-speed spotting instrument was used for spotting the protein samples (antibodies against the proteins of the present invention) in the multi-well plate on the PDVF film. There are 15 sample spots (ibid) for each array, and the diameter of each sample spot is 0.4 mm;

(2) the film was washed for 2-3 times with buffer solution, 3-6 minutes for each time;

(3) 5% calf serum or skimmed milk powder was used for blockage for 1-2 hours at room temperature;

(4) the film was washed for 2-3 times with buffer solution again, 3-6 minutes for each time;

(5) the film was dried, sealed with photophobic materials and stored under 4° C.

c Liquid Chip No. 3

(1) A pair of antibodies against the test proteins was prepared, one of them was used as a capture antibodies, and the other was used as a detection antibodies.

(2) Coupling the capture antibody to the magnetic beads. One capture antibody corresponded to a serial number of beads.

(3) The detection antibodies were labeled with fluorescence.

(4) The capture antibodies and detection antibodies were optimized and sorted, in order to prevent cross-reaction occurring between the different proteins to be tested.

Example 6 Formula and Preparation Process for Suppository 5.1 Formula

| composition | amount |
| --- | --- |
| HSPA5 protein | 5 mg |
| β-CD | 10 mg |
| Tween 80 | 2 mg |
| semi-synthetic fatty acid enzyme type 36 | 40 mg |

5.2 Preparation Process:

1. Suitable amount of ethanol were added into β-CD and the product were stirred homogenously to form a paste. HSPA5 protein was added, grinded for clathration for 45 minutes, ready to use.

2. The semi-synthetic fatty acid enzyme type 36 was heated to dissolve, and the temperature was maintained as 38° C. The clathration of the main drug, tween 80 were added, stirred to homogenous and subjected to insulation.

3. The insulated product which was mixed to homogenous was filled into mould and cooled for molding.

Example 8 Preparation of Drugs for Improving In Vitro Fertilization Success Rate The proteins with lower-content were determined by detecting the content of 15 above-mentioned proteins on sperms for in vitro fertilization. The sperm localization proteins obtained from Example 2 or a composition containing various of proteins were subjected to a sperm capacitation liquid, and then the fertilization process of sperms and eggs was completed in the protein-containing capacitation liquid. For the patients suffering male infertility disorders and asthenozoospermia, sperm motility was improved 30 minutes after the proteins had been added, and the number of progressive sperms was increased as well, therefore, the success rate of fertilization in vitro was improved.

Example 9 Quantitative Detection for mRNAs Corresponding to Sperm Localization Proteins Semen samples from 30±5 years old of normal young people, asthenozoospermia patients, oligo asthenozoospermia patients, and 70±2 years old of the old were collected, 10 cases for each group. The samples were washed with PBS for three times and subjected to microscopic counting. Sperm RNA was extracted from the centrifuged sperm by Trizol. The sperm RNA samples were screened with CD52 and CDH1 genes and then subjected to Real-time PCR.

Three parallel experiments were performed on each sample. The reactions were performed according to the instruction of Platinum® SYBR® Green qPCR SuperMix-UDG reaction kit (Invitrogen). The fluorescence quantitative PCR was performed using Rotor-Gene Q (QIAGEN). Reaction condition: 50° C. for 10 min, 95° C. for 10 min, 95° C. for 15 s, 60° C. for 45 s, 40 cycles. The relative expression level of the target gene was calculated using the 2-ΔΔCT method (Kenneth J, et al). ΔΔCT=(Ct(target gene of the test group)−Ct(reference gene of the test group))−(Ct(target gene of the control group)−Ct (reference gene of the control group)). GAPDH was selected as the reference gene.

Figure 6:
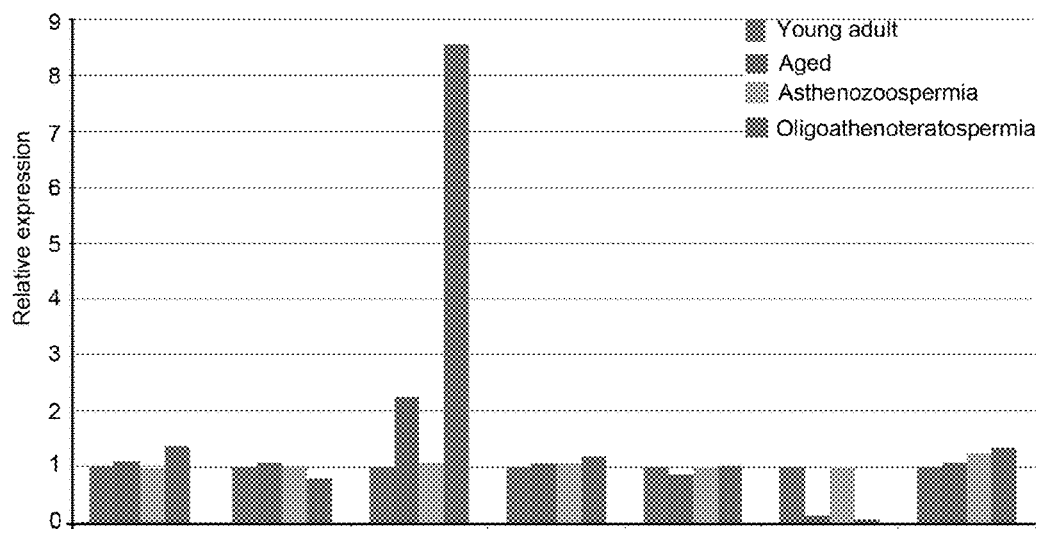
FIG. 6 shows a quantitative determination result of 7 age-related sperm localization protein mRNAs in the sperm from different origins. Young adult refers to the normal young people, Aged refers to the old, Asthenozoospermia refers to patients with Oligospermia, Oligo asthenozoospermia refers to patients with Oligoasthenotspermia.

Using the above method, the mRNA transcription levels of 15 genes in Table 1 in normal sperms from the young people were detected, and as a result, 7 genes can be detected. The transcription levels of them in the sperms from the old, the asthenozoospermia, and the oligo asthenozoospermia were further analysed. It was found that the level of mRNA of AK6 in the sperms from the old was twice as much as that from the normal young, the level of mRNA of AK6 in the sperms of the oligo asthenozoospermia was 8 times as much as that from the normal young, the level of mRNA of GPX5 in the sperms from the old is 0.12 times as much as that from the normal young, the level of mRNA of GPX5 in the sperms from the oligo asthenozoospermia is 0.07 times as much as that from the normal young. The contents of mRNAs of UAP1, CTSB, HSPA1L, HSPA5, or CALR in the sperms from the normal young and the old, the asthenozoospermia, and the oligo asthenozoospermia are not significantly different. The statistical results are shown in FIG. 6.

Figure 7:
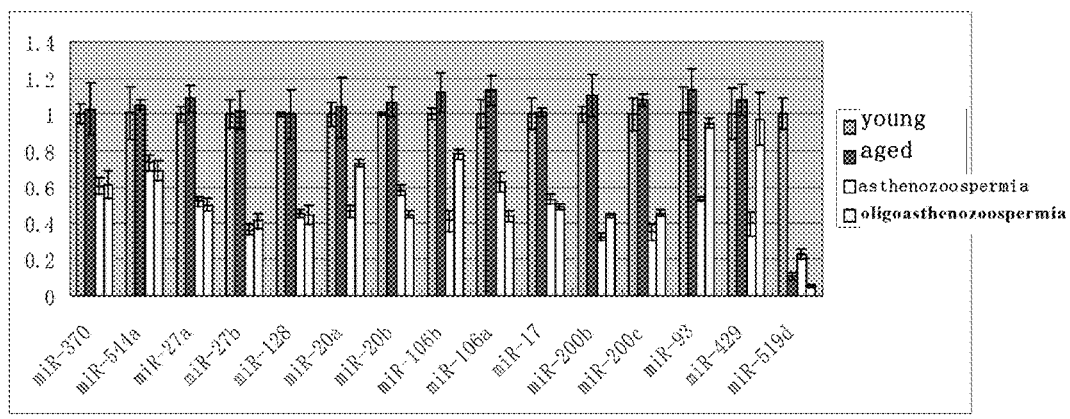
FIG. 7 shows a qRT-PCR analytical result of 15 AK6 regulatory related miRNA expressed in sperms of young adult, aged, asthenozoospermia and oligo asthenozoospermia.

Example 10 Quantitative Detection of AK6 Gene Regulatory-Associated miRNA on Sperms Two softwares, TargetScan (http://www.targetscan.org/) and miRanda (http://www.microrna.org/microrna/home.do), were simultaneously used to predict miRNA molecules that regulate AK6 transcription. TargetScan predicted 53 miRNAs and miRanda predicted 17 miRNAs, wherein 15 miRNAs were overlapped in two databases. The quantitative detection of the levels of the 15 miRNAs on sperms was carried out. The method was shown below: The total RNA was extracted from 10 sperms devoted from the normal population, the asthenozoospermia, the old (70±2 years), and the oligo asthenozoospermia, respectively. For each miRNA reverse transcription reaction, miRNA-specific stem-loop primers, 1 ng-1 µg of total RNA, and ReverTra Ace reverse transcriptase (Toyobo) were used. PCR was performed using miRNA-specific forward primers and universal reverse primer (URP) with QIAGEN's Roter-Gene Q. In a 20 µL reaction system, 1 µL cDNA template was included. The PCR condition was: 95° C. for 5 minutes, 95° C. for 10 seconds, and 60° C. for 45 seconds, 40 cycles in total. The enzyme used in the PCR was Platinum SYBR Green qPCR SuperMix-UDG, commercially available from Life Technologies (Cat. No. 11733-038). U6 snRNA was used as a reference gene. The $2^{-\Delta\Delta Ct}$ method was used to calculate the difference in miRNA levels between the samples. All experiments were done triplicated. The results are shown in FIG. 7.

The results shows that compared with the normal sperms group, the expressions of miR-370, miR-544a, miR-27a, miR-27b, miR-128, miR-20a, miR-20b, miR-106b, miR-106a, miR-17, miR-200b, and miR-200c were decreased in the oligo asthenozoospermia group, the expressions of miR-93 and miR-429 were decreased in the asthenozoospermia group, the expression of miR-519d was significantly decreased in the old, the asthenozoospermia and the oligo asthenozoospermia patients. It is expected to achieve the auxiliary diagnosis for oligozoospermia and male infertility, etc. by quantitatively detecting these 15 miRNAs.

Figure 8:
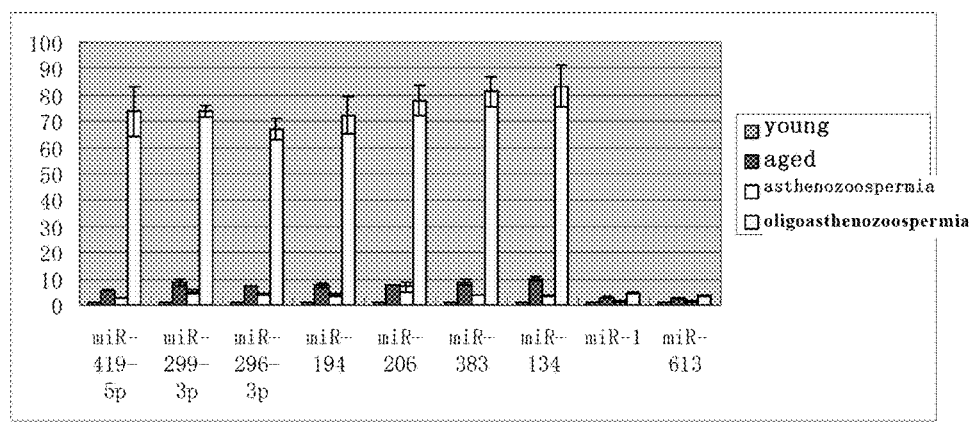
FIG. 8 shows a qRT-PCR analytical result of 9 GPX5 regulatory related miRNA expressed in sperms of young adult, aged, asthenozoospermia and oligo asthenozoospermia.

Example 11 Quantitative Detection of GPX5 Gene Regulatory-Associated miRNA on Sperms The prediction of GPX5 transcriptional regulation-related miRNAs and the quantitative detection method thereof on sperms were the same as in Example 11. 9 GPX5 transcriptional regulation-related miRNAs were predicted, and the quantitative detection results thereof in the sperms from the normal young, the old (70±2 years), the asthenozoospermia, the oligo asthenozoospermia were shown in FIG. 8.

The results show that compared with the normal sperms group, the expressions of the 9 miRNAs in the old and the oligo asthenozoospermia patients were increased at least by 2.5 times. Wherein the expressions of miR-419-5p, miR-299-3p, miR-296-3p, miR-194, miR-134, miR-383, and miR-206 in the oligo asthenozoospermia group were increased at least by 66 times, and were increased in the asthenozoospermia group at least by 2.4 times.

Discussion

At present, a few of seminal plasma proteins have been used for the auxiliary diagnosis and treatment of infertility Combined detection with a number of markers can screen and improve the positive rate of the diagnosis. Commonly used immunological detection methods include radioimmunoassay (RIA), enzyme-linked immunosorbent assay (ELISA), or chemiluminescence immunoassay (CLIA). Although these techniques have their own advantages, all of these techniques have a common limitation, that is, only one infertility protein marker can be detected for each time, which obviously fails to meet the clinical need for the combined detection of multiple markers of infertility. Gene chips and protein chips can not only be used to analyze a variety of different genes or proteins simultaneously in the same samples, but also detect multiple samples at the same time. Therefore, the work efficiency can be greatly improved additionally with high sensitivity and accuracy, good signal to noise ratio, and only a small sample is needed. It is easy to operate and the repeatability is good.

15 age-related human sperm localization proteins, molecular biological materials thereof, such as genes, antibodies, mRNA, and miRNAs which regulate the transcription of these genes, including interference RNA, any fragments of proteins or genes, vaccine, etc. were screened and obtained by the present invention for the first time. A detection method for the transcription level, expression level, gene mutation, amino acid variations, adding and deleting, regulation for the associated miRNA level, antibodies of one or more genes selected from 15 male fertility-associated proteins is established, and a pharmaceutical composition containing one or more proteins in Table 1 and AK6 is prepared. In addition, based on proteomics of testis and epididymal sperm maturation microenvironment, proteomic analysis of testis and epididymis 2D-DIGE differential proteomics of different age groups and protein immunofluorescence localization and quantification of sperms were conducted. The results show that the quantitative localization of 15 proteins in the sperms of the old is significantly different from that of the young adults (wherein 14 of which are significantly decreased and 1 is significantly increased). In addition, the difference will be more significant with aging, indicating that senile sperm dysfunction or loss of function is associated with these sperm localization proteins, in particular with the reduction of the 14 down-regulated expression proteins or the reduction of the 14 down-regulated expression proteins will lead to impaired fertility or loss of function to some extent. The present invention contributes to promote the development of the medical technology related with the diagnosis, treatment, prevention for the male infertility, and the development of the diagnostic agents, therapeutic agents, prophylactic drugs and contraceptives. The present invention also contributes to promote the development of anti-aging products and medical cosmetic technologies.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A method for detecting or diagnosing male infertility and improving in vitro fertilization success rate comprising:
   (i) detecting expression and/or activity of a protein set or a gene set thereof in a sample from a test subject, wherein the protein set comprises: (a) AK6 protein, and optionally (b) one or more proteins listed in Table 1 and selected from the group consisting of LMNB2, HADH, UAP1, CALR, AKR7A2, CTSB, HSPA5, GPX5, KLHL15, HSPA1L, GP83, CLDN7, ALDH4A1, and ALDH2;
   (ii) determining whether the test subject has a higher probability of infertility than normal population by satisfying the following relationship:
   the ratio of the expression and/or activity of AK6 gene or protein in the sample from the test subject to the expression and/or the activity of AK6 gene or protein in normal population is ≥2; and/or
   the ratio of the expression and/or activity of one or more proteins selected from the group consisting of SEQ ID NOs.: 4, 6, 8, 10, 12, 14, 16, 18, 20, 22, 24, 26, 28, and 30 in Table 1 in the sample from the test subject to the expression and/or the activity of that in normal population is ≤0.5;
   (iii) contacting in vitro a sperm capacitation liquid with one or more proteins listed in Table 1 and selected from the group consisting of LMNB2, HADH, UAP1, CALR, AKR7A2, CTSB, HSPA5, GPX5, KLHL15, HSPA1L, GP83, CLDN7, ALDH4A1, and ALDH2, and completing an in vitro fertilization process of sperms and eggs, wherein the sperm capacitation liquid contains the sperms from the test subject whose probability of infertility is higher than normal population.

2. The method of claim 1, wherein in step (i), further comprising detecting AK6 regulatory miRNA.

3. The method of claim 2, wherein a low expression of the AK6 regulatory miRNA indicates that the test subject has a higher probability of infertility than normal population.

4. The method of claim 2, wherein the AK6 regulatory miRNA is selected from the group consisting of miR-370, miR-544a, miR-27a, miR-27b, miR-128, miR-20a, miR-20b, miR-106b, miR-106a, miR-17, miR-200b, miR-200c, miR-93, miR-429, and miR-519d.

5. The method of claim 4 wherein in step (ii), if the expression of one or more microRNAs of miR-370, miR-544a, miR-27a, miR-27b, miR-128, miR-20a, miR-20b, miR-106b, miR-106a, miR-17, miR-200b, and miR-200c are decreased as compared with normal population, it indicates that the subject suffers from oligospermia.

6. The method of claim 4 wherein in step (ii), if the expression of miR-93 and miR-429 are decreased as compared with normal population, it indicates that the subject suffers from oligospermia.

7. The method of claim 4 wherein in step (ii), if the expression of miR-519d is significantly decreased as compared with normal population, it indicates that the subject suffers from asthenozoospermia or oligospermia.

8. The method of claim 1, wherein in step (i) further comprising detecting GPX5 regulatory miRNA, wherein the GPX5 regulatory miRNA selected from the group consisting of miR-419-5p, miR-299-3p, miR-296-3p, miR-194, miR-134, miR-383, and miR-206.

* * * * *

SEQUENCE LISTING

<160> NUMBER OF SEQ ID NOS: 52

<210> SEQ ID NO 1
<211> LENGTH: 519
<212> TYPE: DNA
<213> ORGANISM: Homo sapiens

<400> SEQUENCE: 1

| | | | | | |
|---|---|---|---|---|---|
| atgttgcttc | cgaacatcct | gctcaccggt | acaccagggg | ttggaaaaac | cacactaggc | 60 |
| aaagaacttg | cgtcaaaatc | aggactgaaa | tacattaatg | tgggtgattt | agctcgagaa | 120 |
| gagcaattgt | atgatggcta | tgatgaagag | tatgactgtc | ccattttaga | tgaagacaga | 180 |
| gtagttgatg | agttagataa | ccaaatgaga | gaaggtggag | ttattgttga | ttaccatggt | 240 |
| tgtgatttct | tccctgaacg | ctggtttcat | atagttttg | tgctgagaac | agataccaat | 300 |
| gtattgtacg | aaagacttga | aacaaggggt | tataatgaga | gaaaactaac | agacaatatt | 360 |
| cagtgtgaga | tttttcaagt | tctttatgaa | gaagccacag | catcctacaa | ggaagaaatc | 420 |
| gtgcatcagc | tgcccagtaa | taaaccagaa | gagctagaaa | ataatgtaga | tcagatcttg | 480 |
| aaatggattg | agcagtggat | caaagatcat | aactcttga | | | 519 |

<210> SEQ ID NO 2
<211> LENGTH: 172
<212> TYPE: PRT
<213> ORGANISM: Homo sapiens

<400> SEQUENCE: 2

Met Leu Leu Pro Asn Ile Leu Leu Thr Gly Thr Pro Gly Val Gly Lys
1               5                   10                  15

Thr Thr Leu Gly Lys Glu Leu Ala Ser Lys Ser Gly Leu Lys Tyr Ile
            20                  25                  30

Asn Val Gly Asp Leu Ala Arg Glu Glu Gln Leu Tyr Asp Gly Tyr Asp
        35                  40                  45

Glu Glu Tyr Asp Cys Pro Ile Leu Asp Glu Asp Arg Val Val Asp Glu
    50                  55                  60

Leu Asp Asn Gln Met Arg Glu Gly Gly Val Ile Val Asp Tyr His Gly
65                  70                  75                  80

Cys Asp Phe Phe Pro Glu Arg Trp Phe His Ile Val Phe Val Leu Arg
                85                  90                  95

Thr Asp Thr Asn Val Leu Tyr Glu Arg Leu Glu Thr Arg Gly Tyr Asn
            100                 105                 110

Glu Lys Lys Leu Thr Asp Asn Ile Gln Cys Glu Ile Phe Gln Val Leu
        115                 120                 125

Tyr Glu Glu Ala Thr Ala Ser Tyr Lys Glu Glu Ile Val His Gln Leu
    130                 135                 140

Pro Ser Asn Lys Pro Glu Glu Leu Glu Asn Asn Val Asp Gln Ile Leu
145                 150                 155                 160

Lys Trp Ile Glu Gln Trp Ile Lys Asp His Asn Ser
                165                 170

<210> SEQ ID NO 3
<211> LENGTH: 1863
<212> TYPE: DNA
<213> ORGANISM: Homo sapiens

<400> SEQUENCE: 3

| | | | | | |
|---|---|---|---|---|---|
| atgagcccgc | cgagcccggg | ccgccgtcgg | gagcagcgca | ggccgcgagc | cgccgccacc | 60 |

| | | |
|---|---|---|
| atggccacgc cgctgcccgg ccgcgcgggc gggcccgcca cgccgctgtc gcccacgcgc | 120 |
| ctgtcgcggc tgcaggagaa ggaggagctg cgcgagctca acgaccgcct ggcgcactac | 180 |
| atcgaccgcg tccgcgcgct ggagctggag aacgaccggc tcctgctcaa gatctcagag | 240 |
| aaggaggagg tgaccacgcg cgaggtgagt ggcatcaagg cgctgtacga gtcggagctg | 300 |
| gccgatgccc ggagagtcct ggatgagacg gctcgagagc gtgcccggct gcagatagag | 360 |
| attgggaagc tgagggcaga gttggacgag gtcaacaaga gcgccaagaa gagggagggc | 420 |
| gagcttacgg tggcccaggg ccgtgtgaag gacctggagt ccctgttcca ccggagcgag | 480 |
| gtggagctgg cagctgccct cagcgacaag gcgggcctgg agagtgacgt ggctgagctg | 540 |
| cgggcccagc tggccaaggc cgaggacggt catgcagtgg ccaaaaagca gctggagaag | 600 |
| gagacgctga tgcgtgtgga cctggagaac cgctgccaga gcctgcagga ggagctggac | 660 |
| ttccggaaga gtgtgttcga ggaggaggtg cgggagacgc ggcggcggca cgagcggcgc | 720 |
| ctggtggagg tggacagcag ccggcagcag gagtacgact tcaagatggc acaggcgctg | 780 |
| gaggagctgc ggagccagca cgacgagcaa gtgcggctct acaagctgga gctggagcag | 840 |
| acctaccagg ccaagctgga cagcgccaag ctgagctctg accagaacga caaggcggcc | 900 |
| agtgcggctc gcgaggagct gaaggaggcc cgcatgcgcc tggagtccct cagctaccag | 960 |
| ctctccggcc tccagaagca ggccagtgcc gctgaagatc gcattcggga gctggaggag | 1020 |
| gccatggccg gggagcggga caagttccgg aagatgctgg acgccaagga gcaggagatg | 1080 |
| acggagatgc gggacgtgat gcagcagcag ctggccgagt accaggagct gctggacgtg | 1140 |
| aagctggccc tggacatgga gatcaacgcc taccggaagc cctggagggg cgaggaggag | 1200 |
| aggctgaagc tgtcccccag cccatcctcg cgcgtcaccg tctcacgagc cacctcgagc | 1260 |
| agcagcggca gcttgtccgc caccgggcgc ctgggccgca gtaagcggaa gcggctggag | 1320 |
| gtggaggagc ccttgggcag cggcccaagc gtcctgggca cgggcacggg tggcagcggt | 1380 |
| ggcttccacc tggcccagca ggcctcggcc tcgggtagcg tcagcatcga ggagatcgac | 1440 |
| ctggagggca gtttgtgca gctcaagaac aactcggaca aggatcagtc tctggggaac | 1500 |
| tggagaatca agaggcaggt cttggagggg gaggagatcg cctacaagtt cacgcccaag | 1560 |
| tacatcctgc gcgccggcca gatggtcacg gtgtgggcag ctggtgcggg ggtggcccac | 1620 |
| agccccccct cgacgctggt gtggaagggc cagagcagct ggggcacggg cgagagcttc | 1680 |
| cgcaccgtcc tggttaacgc ggatggcgag gaagtggcca tgaggactgt gaagaagtcc | 1740 |
| tcggtgatgc gtgagaatga gaatggggag gaagaggagg aggaagccga gtttggcgag | 1800 |
| gaggatcttt tccaccaaca gggggacccg aggaccacct caagaggctg ctacgtgatg | 1860 |
| tga | 1863 |

<210> SEQ ID NO 4
<211> LENGTH: 620
<212> TYPE: PRT
<213> ORGANISM: Homo sapiens

<400> SEQUENCE: 4

Met Ser Pro Pro Ser Pro Gly Arg Arg Glu Gln Arg Arg Pro Arg
1               5                   10                  15

Ala Ala Ala Thr Met Ala Thr Pro Leu Pro Gly Arg Ala Gly Gly Pro
                20                  25                  30

Ala Thr Pro Leu Ser Pro Thr Arg Leu Ser Arg Leu Gln Glu Lys Glu
            35                  40                  45

Glu Leu Arg Glu Leu Asn Asp Arg Leu Ala His Tyr Ile Asp Arg Val
50                  55                  60

Arg Ala Leu Glu Leu Glu Asn Asp Arg Leu Leu Lys Ile Ser Glu
65                  70                  75                  80

Lys Glu Glu Val Thr Thr Arg Glu Val Ser Gly Ile Lys Ala Leu Tyr
                85                  90                  95

Glu Ser Glu Leu Ala Asp Ala Arg Arg Val Leu Asp Glu Thr Ala Arg
                100                 105                 110

Glu Arg Ala Arg Leu Gln Ile Glu Ile Gly Lys Leu Arg Ala Glu Leu
                115                 120                 125

Asp Glu Val Asn Lys Ser Ala Lys Lys Arg Glu Gly Glu Leu Thr Val
130                 135                 140

Ala Gln Gly Arg Val Lys Asp Leu Glu Ser Leu Phe His Arg Ser Glu
145                 150                 155                 160

Val Glu Leu Ala Ala Ala Leu Ser Asp Lys Arg Gly Leu Glu Ser Asp
                165                 170                 175

Val Ala Glu Leu Arg Ala Gln Leu Ala Lys Ala Glu Asp Gly His Ala
                180                 185                 190

Val Ala Lys Lys Gln Leu Glu Lys Glu Thr Leu Met Arg Val Asp Leu
                195                 200                 205

Glu Asn Arg Cys Gln Ser Leu Gln Glu Glu Leu Asp Phe Arg Lys Ser
210                 215                 220

Val Phe Glu Glu Glu Val Arg Glu Thr Arg Arg Arg His Glu Arg Arg
225                 230                 235                 240

Leu Val Glu Val Asp Ser Ser Arg Gln Gln Glu Tyr Asp Phe Lys Met
                245                 250                 255

Ala Gln Ala Leu Glu Glu Leu Arg Ser Gln His Asp Glu Gln Val Arg
                260                 265                 270

Leu Tyr Lys Leu Glu Leu Glu Gln Thr Tyr Gln Ala Lys Leu Asp Ser
                275                 280                 285

Ala Lys Leu Ser Ser Asp Gln Asn Asp Lys Ala Ala Ser Ala Ala Arg
                290                 295                 300

Glu Glu Leu Lys Glu Ala Arg Met Arg Leu Glu Ser Leu Ser Tyr Gln
305                 310                 315                 320

Leu Ser Gly Leu Gln Lys Gln Ala Ser Ala Ala Glu Asp Arg Ile Arg
                325                 330                 335

Glu Leu Glu Glu Ala Met Ala Gly Glu Arg Asp Lys Phe Arg Lys Met
                340                 345                 350

Leu Asp Ala Lys Glu Gln Glu Met Thr Glu Met Arg Asp Val Met Gln
                355                 360                 365

Gln Gln Leu Ala Glu Tyr Gln Glu Leu Leu Asp Val Lys Leu Ala Leu
                370                 375                 380

Asp Met Glu Ile Asn Ala Tyr Arg Lys Leu Leu Glu Gly Glu Glu Glu
385                 390                 395                 400

Arg Leu Lys Leu Ser Pro Ser Pro Ser Arg Val Thr Val Ser Arg
                405                 410                 415

Ala Thr Ser Ser Ser Ser Gly Ser Leu Ser Ala Thr Gly Arg Leu Gly
                420                 425                 430

Arg Ser Lys Arg Lys Arg Leu Glu Val Glu Glu Pro Leu Gly Ser Gly
                435                 440                 445

Pro Ser Val Leu Gly Thr Gly Thr Gly Gly Ser Gly Gly Phe His Leu
450                 455                 460

Ala Gln Gln Ala Ser Ala Ser Gly Ser Val Ser Ile Glu Glu Ile Asp

```
                    465                 470                 475                 480
Leu Glu Gly Lys Phe Val Gln Leu Lys Asn Asn Ser Asp Lys Asp Gln
                485                 490                 495

Ser Leu Gly Asn Trp Arg Ile Lys Arg Gln Val Leu Glu Gly Glu Glu
            500                 505                 510

Ile Ala Tyr Lys Phe Thr Pro Lys Tyr Ile Leu Arg Ala Gly Gln Met
        515                 520                 525

Val Thr Val Trp Ala Ala Gly Val Ala His Ser Pro Pro Ser
    530                 535                 540

Thr Leu Val Trp Lys Gly Gln Ser Ser Trp Gly Thr Gly Glu Ser Phe
545                 550                 555                 560

Arg Thr Val Leu Val Asn Ala Asp Gly Glu Glu Val Ala Met Arg Thr
                565                 570                 575

Val Lys Lys Ser Ser Val Met Arg Glu Asn Glu Asn Gly Glu Glu Glu
            580                 585                 590

Glu Glu Glu Ala Glu Phe Gly Glu Glu Asp Leu Phe His Gln Gln Gly
        595                 600                 605

Asp Pro Arg Thr Thr Ser Arg Gly Cys Tyr Val Met
    610                 615                 620

<210> SEQ ID NO 5
<211> LENGTH: 945
<212> TYPE: DNA
<213> ORGANISM: Homo sapiens

<400> SEQUENCE: 5
atggccttcg tcaccaggca gttcatgcgt tccgtgtcct cctcgtccac cgcctcggcc        60
tcggccaaga gataatcgt caagcacgtg acggtcatcg gcggcgggct gatgggcgcc       120
ggcattgccc aggttgctgc agcaactggt cacacagtag tgttggtaga ccagacagag       180
gacatcctgg caaaatccaa aaagggaatt gaggaaagcc ttaggaaagt ggcaaagaag       240
aagtttgcag aaaaccttaa ggccggcgat gaatttgtgg agaagaccct gagcaccata       300
gcgaccagca cggatgcagc ctccgttgtc cacagcacag acttggtggt ggaagccatc       360
gtggagaatc tgaaggtgaa aaacgagctc ttcaaaaggc tggacaagtt tgctgctgaa       420
catacaatct tgccagcaa cacttcctcc ttgcagatta caagcatagc taatgccacc       480
accagacaag accgattcgc tggcctccat ttcttcaacc cagtgcctgt catgaaactt       540
gtggaggtca ttaaaacacc aatgaccagc cagaagacat tgaatctttt ggtagacttt       600
agcaaagccc taggaaagca tcctgttct tgcaaggaca ctcctgggtt tattgtgaac       660
cgcctcctgg ttccatacct catggaagca atcaggctgt atgaacgagg tgacgcatcc       720
aaagaagaca ttgacactgc tatgaaatta ggagccggtt accccatggg cccatttgag       780
cttctagatt atgtcggact ggatactacg aagttcatcg tggatgggtg gcatgaaatg       840
gatgcagaga acccattaca tcagcccagc ccatccttaa ataagctggt agcagagaac       900
aagttcggca agaagactgg agaaggattt tacaaataca agtga                      945

<210> SEQ ID NO 6
<211> LENGTH: 314
<212> TYPE: PRT
<213> ORGANISM: Homo sapiens

<400> SEQUENCE: 6

Met Ala Phe Val Thr Arg Gln Phe Met Arg Ser Val Ser Ser Ser Ser
1               5                   10                  15
```

```
Thr Ala Ser Ala Ser Ala Lys Lys Ile Ile Val Lys His Val Thr Val
             20                  25                  30
Ile Gly Gly Gly Leu Met Gly Ala Gly Ile Ala Gln Val Ala Ala Ala
         35                  40                  45
Thr Gly His Thr Val Val Leu Val Asp Gln Thr Glu Asp Ile Leu Ala
     50                  55                  60
Lys Ser Lys Lys Gly Ile Glu Glu Ser Leu Arg Lys Val Ala Lys Lys
 65                  70                  75                  80
Lys Phe Ala Glu Asn Leu Lys Ala Gly Asp Glu Phe Val Glu Lys Thr
                 85                  90                  95
Leu Ser Thr Ile Ala Thr Ser Thr Asp Ala Ala Ser Val Val His Ser
            100                 105                 110
Thr Asp Leu Val Val Glu Ala Ile Val Glu Asn Leu Lys Val Lys Asn
        115                 120                 125
Glu Leu Phe Lys Arg Leu Asp Lys Phe Ala Ala Glu His Thr Ile Phe
130                 135                 140
Ala Ser Asn Thr Ser Ser Leu Gln Ile Thr Ser Ile Ala Asn Ala Thr
145                 150                 155                 160
Thr Arg Gln Asp Arg Phe Ala Gly Leu His Phe Phe Asn Pro Val Pro
                165                 170                 175
Val Met Lys Leu Val Glu Val Ile Lys Thr Pro Met Thr Ser Gln Lys
            180                 185                 190
Thr Phe Glu Ser Leu Val Asp Phe Ser Lys Ala Leu Gly Lys His Pro
        195                 200                 205
Val Ser Cys Lys Asp Thr Pro Gly Phe Ile Val Asn Arg Leu Leu Val
210                 215                 220
Pro Tyr Leu Met Glu Ala Ile Arg Leu Tyr Glu Arg Gly Asp Ala Ser
225                 230                 235                 240
Lys Glu Asp Ile Asp Thr Ala Met Lys Leu Gly Ala Gly Tyr Pro Met
                245                 250                 255
Gly Pro Phe Glu Leu Leu Asp Tyr Val Gly Leu Asp Thr Thr Lys Phe
            260                 265                 270
Ile Val Asp Gly Trp His Glu Met Asp Ala Glu Asn Pro Leu His Gln
        275                 280                 285
Pro Ser Pro Ser Leu Asn Lys Leu Val Ala Glu Asn Lys Phe Gly Lys
290                 295                 300
Lys Thr Gly Glu Gly Phe Tyr Lys Tyr Lys
305                 310
```

<210> SEQ ID NO 7
<211> LENGTH: 1518
<212> TYPE: DNA
<213> ORGANISM: Homo sapiens

<400> SEQUENCE: 7

```
atgaacatta tgacctcaa actcacgttg tccaaagctg gcaagagca cctactacgt      60 ttctggaatg agcttgaaga agcccaacag gtagaacttt atgcagagct ccaggccatg    120
aactttgagg agctgaactt ctttttccaa aaggccattg aaggttttaa ccagtcttct    180
caccaaaaga atgtggatgc acgaatggaa cctgtgcctc gagaggtatt aggcagtgct    240
acaagggatc aagatcagct ccaggcctgg gaaagtgaag acttttcca gatttctcag     300 aataaagtag cagttcttct tctagctggt gggcagggga caagactcgg cgttgcatat    360
cctaagggga tgtatgatgt tggtttgcca tcccgtaaga cacttttca gattcaagca    420
```

```
gagcgtatcc tgaagctaca gcaggttgct gaaaaatatt atggcaacaa atgcattatt    480
ccatggtata taatgaccag tggcagaaca atggaatcta caaggagtt cttcaccaag     540 cacaagtact ttggtttaaa aaagagaat gtaatctttt ttcagcaagg aatgctcccc    600
gccatgagtt ttgatgggaa aattattttg gaagagaaga acaaagtttc tatggctcca   660
gatgggaatg gtggtcttta tcgggcactt gcagcccaga atattgtgga ggatatggag   720
caaagaggca tttggagcat tcatgtctat tgtgttgaca acatattagt aaagtggca    780 gacccacggt tcattggatt ttgcattcag aaaggagcag actgtggagc aaaggtggta   840
gagaaaacga accctacaga accagttgga gtggtttgcc gagtggatgg agtttaccag   900
gtggtagaat atagtgagat tccctggca acagctcaaa aacgaagctc agacggacga    960
ctgctgttca atgcgggaa cattgccaac catttcttca ctgtaccatt tctgagagat   1020
gttgtcaatg tttatgaacc tcagttgcag caccatgtgg ctcaaaagaa gattccttat  1080
gtggataccc aaggacagtt aattaagcca gacaaaccca atggaataaa gatggaaaaa  1140
tttgtctttg acatcttcca gtttgcaaag aagtttgtgg tatatgaagt attgcgagaa  1200
gatgagtttt ccccactaaa gaatgctgat agtcagaatg ggaaagacaa ccctactact  1260
gcaaggcatg ctttgatgtc ccttcatcat tgctgggtcc tcaatgcagg gggccatttc  1320
atagatgaaa atggctctcg ccttccagca attccccgct tgaaggatgc caatgatgta  1380
ccaatccaat gtgaaatctc tcctcttatc tcctatgctg gagaaggatt agaaagttat  1440
gtggcagata aagaattcca tgcacctcta atcatcgatg agaatggagt tcatgagctg  1500
gtgaaaaatg gtatttga                                                1518

<210> SEQ ID NO 8
<211> LENGTH: 505
<212> TYPE: PRT
<213> ORGANISM: Homo sapiens

<400> SEQUENCE: 8

Met Asn Ile Asn Asp Leu Lys Leu Thr Leu Ser Lys Ala Gly Gln Glu
1               5                   10                  15

His Leu Leu Arg Phe Trp Asn Glu Leu Glu Glu Ala Gln Gln Val Glu
            20                  25                  30

Leu Tyr Ala Glu Leu Gln Ala Met Asn Phe Glu Glu Leu Asn Phe Phe
        35                  40                  45

Phe Gln Lys Ala Ile Glu Gly Phe Asn Gln Ser His Gln Lys Asn
    50                  55                  60

Val Asp Ala Arg Met Glu Pro Val Pro Arg Glu Val Leu Gly Ser Ala
65                  70                  75                  80

Thr Arg Asp Gln Asp Gln Leu Gln Ala Trp Glu Ser Glu Gly Leu Phe
                85                  90                  95

Gln Ile Ser Gln Asn Lys Val Ala Val Leu Leu Leu Ala Gly Gly Gln
            100                 105                 110

Gly Thr Arg Leu Gly Val Ala Tyr Pro Lys Gly Met Tyr Asp Val Gly
        115                 120                 125

Leu Pro Ser Arg Lys Thr Leu Phe Gln Ile Gln Ala Glu Arg Ile Leu
    130                 135                 140

Lys Leu Gln Gln Val Ala Glu Lys Tyr Tyr Gly Asn Lys Cys Ile Ile
145                 150                 155                 160

Pro Trp Tyr Ile Met Thr Ser Gly Arg Thr Met Glu Ser Thr Lys Glu
                165                 170                 175
```

```
Phe Phe Thr Lys His Lys Tyr Phe Gly Leu Lys Lys Glu Asn Val Ile
            180                 185                 190
Phe Phe Gln Gln Gly Met Leu Pro Ala Met Ser Phe Asp Gly Lys Ile
            195                 200                 205
Ile Leu Glu Glu Lys Asn Lys Val Ser Met Ala Pro Asp Gly Asn Gly
            210                 215                 220
Gly Leu Tyr Arg Ala Leu Ala Ala Gln Asn Ile Val Glu Asp Met Glu
225                 230                 235                 240
Gln Arg Gly Ile Trp Ser Ile His Val Tyr Cys Val Asp Asn Ile Leu
                    245                 250                 255
Val Lys Val Ala Asp Pro Arg Phe Ile Gly Phe Cys Ile Gln Lys Gly
            260                 265                 270
Ala Asp Cys Gly Ala Lys Val Val Glu Lys Thr Asn Pro Thr Glu Pro
            275                 280                 285
Val Gly Val Val Cys Arg Val Asp Gly Val Tyr Gln Val Val Glu Tyr
            290                 295                 300
Ser Glu Ile Ser Leu Ala Thr Ala Gln Lys Arg Ser Ser Asp Gly Arg
305                 310                 315                 320
Leu Leu Phe Asn Ala Gly Asn Ile Ala Asn His Phe Phe Thr Val Pro
                    325                 330                 335
Phe Leu Arg Asp Val Val Asn Val Tyr Glu Pro Gln Leu Gln His His
            340                 345                 350
Val Ala Gln Lys Lys Ile Pro Tyr Val Asp Thr Gln Gly Gln Leu Ile
            355                 360                 365
Lys Pro Asp Lys Pro Asn Gly Ile Lys Met Glu Lys Phe Val Phe Asp
            370                 375                 380
Ile Phe Gln Phe Ala Lys Lys Phe Val Val Tyr Glu Val Leu Arg Glu
385                 390                 395                 400
Asp Glu Phe Ser Pro Leu Lys Asn Ala Asp Ser Gln Asn Gly Lys Asp
                    405                 410                 415
Asn Pro Thr Thr Ala Arg His Ala Leu Met Ser Leu His His Cys Trp
            420                 425                 430
Val Leu Asn Ala Gly Gly His Phe Ile Asp Glu Asn Gly Ser Arg Leu
            435                 440                 445
Pro Ala Ile Pro Arg Leu Lys Asp Ala Asn Asp Val Pro Ile Gln Cys
            450                 455                 460
Glu Ile Ser Pro Leu Ile Ser Tyr Ala Gly Glu Gly Leu Glu Ser Tyr
465                 470                 475                 480
Val Ala Asp Lys Glu Phe His Ala Pro Leu Ile Ile Asp Glu Asn Gly
                    485                 490                 495
Val His Glu Leu Val Lys Asn Gly Ile
            500                 505

<210> SEQ ID NO 9
<211> LENGTH: 1254
<212> TYPE: DNA
<213> ORGANISM: Homo sapiens

<400> SEQUENCE: 9
atgctgctat ccgtgccgct gctgctcggc ctcctcggcc tggccgtcgc cgagcctgcc    60
gtctacttca aggagcagtt tctggacgga gacgggtgga cttcccgctg atcgaatcc    120 aaacacaagt cagattttgg caaattcgtt ctcagttccg gcaagttcta cggtgacgag    180
gagaaagata aggtttgca gacaagccag gatgcacgct tttatgctct gtcggccagt    240
```

-continued

```
ttcgagcctt tcagcaacaa aggccagacg ctggtggtgc agttcacggt gaaacatgag      300
cagaacatcg actgtggggg cggctatgtg aagctgtttc ctaatagttt ggaccagaca      360
gacatgcacg gagactcaga atacaacatc atgtttggtc ccgacatctg tggccctggc      420
accaagaagg ttcatgtcat cttcaactac aagggcaaga acgtgctgat caacaaggac      480
atccgttgca aggatgatga gtttacacac ctgtacacac tgattgtgcg ccagacaac      540 acctatgagg tgaagattga caacagccag gtggagtccg ctccttgga agacgattgg      600 gacttcctgc acccaagaa gataaaggat cctgatgctt caaaaccgga agactgggat      660
gagcgggcca agatcgatga tcccacagac tccaagcctg aggactggga caagcccgag      720
catatccctg accctgatgc taagaagccc gaggactggg atgaagagat ggacggagag      780
tgggaacccc cagtgattca gaaccctgag tacaaggggt gtggaagcc ccggcagatc      840 gacaacccag attacaaggg cacttggatc cacccagaaa ttgacaaccc cgagtattct      900
cccgatccca gtatctatgc ctatgataac tttggcgtgc tgggcctgga cctctggcag      960
gtcaagtctg gcaccatctt tgacaacttc ctcatcacca acgatgaggc atacgctgag     1020
gagtttggca acgagacgtg gggcgtaaca aaggcagcag agaaacaaat gaaggacaaa     1080
caggacgagg agcagaggct taaggaggag gaagaagaca agaaacgcaa agaggaggag     1140
gaggcagagg acaaggagga tgatgaggac aaagatgagg atgaggagga tgaggaggac     1200
aaggaggaag atgaggagga agatgtcccc ggccaggcca aggacgagct gtag           1254
```

<210> SEQ ID NO 10
<211> LENGTH: 417
<212> TYPE: PRT
<213> ORGANISM: Homo sapiens

<400> SEQUENCE: 10

```
Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp
                20                  25                  30

Trp Thr Ser Arg Trp Ile Glu Ser Lys His Lys Ser Asp Phe Gly Lys
                35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
                100                 105                 110

Phe Pro Asn Ser Leu Asp Gln Thr Asp Met His Gly Asp Ser Glu Tyr
            115                 120                 125

Asn Ile Met Phe Gly Pro Asp Ile Cys Gly Pro Gly Thr Lys Lys Val
        130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190
```

Ser Gly Ser Leu Glu Asp Asp Trp Asp Phe Leu Pro Pro Lys Lys Ile
            195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
    290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Glu Ala Glu Asp
    370                 375                 380

Lys Glu Asp Asp Glu Asp Lys Asp Glu Asp Glu Glu Asp Glu Glu Asp
385                 390                 395                 400

Lys Glu Glu Asp Glu Glu Glu Asp Val Pro Gly Gln Ala Lys Asp Glu
                405                 410                 415

Leu

<210> SEQ ID NO 11
<211> LENGTH: 1080
<212> TYPE: DNA
<213> ORGANISM: Homo sapiens

<400> SEQUENCE: 11
atgctgagtg ccgcgtctcg cgtagtctcc cgcgccgccg tccactgcgc gcttcgctct      60
ccgccgcccg aggcccgcgc gctcgccatg tcccggccac cgccaccgcg ggtcgcctcg     120
gtgctgggca ccatggagat ggggcgccgc atggacgcgc cgccagcgc cgcggccgtg     180 cgcgcctttc tggagcgcgg ccacaccgaa ctggacacgg ccttcatgta cagcgacggc     240
cagtccgaga ccatcctggg cggcctgggg ctcgggctgg cggtggcga ctgcagagtg     300 aaaattgcca ccaaggccaa cccttgggat ggaaaatcac taaagcctga cagtgtccgg     360
tcccagctgg agacgtcatt gaagaggctg cagtgtcccc aagtggacct cttctaccta     420
cacgcacctg accacggcac cccggtggaa gagacgctgc atgcctgcca gcggctgcac     480
caggagggca gttcgtgga gcttggcctc tccaactatg ctagctggga agtggccgag     540
atctgtaccc ctgcaagag caatggctgg atcctgccca ctgtgtacca gggcatgtac     600
aacgccacca cccggcaggt ggaaacggag ctcttcccct gcctcaggca ctttggactg     660
aggttctatg cctacaaccc tctggctggg ggcctgctga ctggcaagta caagtatgag     720
gacaaggacg ggaaacagcc tgtggccgc ttctttggga atagctgggc tgagacctac     780
aggaatcgct tctggaagga gcaccacttc gaggccattg cgttggtgga aaggccctg     840

```
caggccgcat atggcgccag cgcccccagt gtgacctcgg ctgccctccg gtggatgtac    900
caccactcac agctgcaggg tgcccacggg gacgcggtca tcctgggcat gtccagcctg    960
gagcagctgg agcagaactt ggcagcaaca gaggaagggc ccctggagcc ggctgtcgtg   1020
gatgccttta tcaagcctg gcatttggtt gctcacgaat gtcccaacta cttccgctag   1080
```

<210> SEQ ID NO 12
<211> LENGTH: 359
<212> TYPE: PRT
<213> ORGANISM: Homo sapiens

<400> SEQUENCE: 12

```
Met Leu Ser Ala Ala Ser Arg Val Val Ser Arg Ala Ala Val His Cys
1               5                   10                  15

Ala Leu Arg Ser Pro Pro Glu Ala Arg Ala Leu Ala Met Ser Arg
            20                  25                  30

Pro Pro Pro Arg Val Ala Ser Val Leu Gly Thr Met Glu Met Gly
            35                  40                  45

Arg Arg Met Asp Ala Pro Ala Ser Ala Ala Val Arg Ala Phe Leu
50                  55                  60

Glu Arg Gly His Thr Glu Leu Asp Thr Ala Phe Met Tyr Ser Asp Gly
65                  70                  75                  80

Gln Ser Glu Thr Ile Leu Gly Gly Leu Gly Leu Gly Leu Gly Gly
            85                  90                  95

Asp Cys Arg Val Lys Ile Ala Thr Lys Ala Asn Pro Trp Asp Gly Lys
                100                 105                 110

Ser Leu Lys Pro Asp Ser Val Arg Ser Gln Leu Glu Thr Ser Leu Lys
            115                 120                 125

Arg Leu Gln Cys Pro Gln Val Asp Leu Phe Tyr Leu His Ala Pro Asp
        130                 135                 140

His Gly Thr Pro Val Glu Glu Thr Leu His Ala Cys Gln Arg Leu His
145                 150                 155                 160

Gln Glu Gly Lys Phe Val Glu Leu Gly Leu Ser Asn Tyr Ala Ser Trp
                165                 170                 175

Glu Val Ala Glu Ile Cys Thr Leu Cys Lys Ser Asn Gly Trp Ile Leu
            180                 185                 190

Pro Thr Val Tyr Gln Gly Met Tyr Asn Ala Thr Thr Arg Gln Val Glu
        195                 200                 205

Thr Glu Leu Phe Pro Cys Leu Arg His Phe Gly Leu Arg Phe Tyr Ala
    210                 215                 220

Tyr Asn Pro Leu Ala Gly Gly Leu Leu Thr Gly Lys Tyr Lys Tyr Glu
225                 230                 235                 240

Asp Lys Asp Gly Lys Gln Pro Val Gly Arg Phe Phe Gly Asn Ser Trp
                245                 250                 255

Ala Glu Thr Tyr Arg Asn Arg Phe Trp Lys Glu His His Phe Glu Ala
            260                 265                 270

Ile Ala Leu Val Glu Lys Ala Leu Gln Ala Ala Tyr Gly Ala Ser Ala
        275                 280                 285

Pro Ser Val Thr Ser Ala Ala Leu Arg Trp Met Tyr His His Ser Gln
    290                 295                 300

Leu Gln Gly Ala His Gly Asp Ala Val Ile Leu Gly Met Ser Ser Leu
305                 310                 315                 320

Glu Gln Leu Glu Gln Asn Leu Ala Ala Thr Glu Glu Gly Pro Leu Glu
                325                 330                 335
```

Pro Ala Val Val Asp Ala Phe Asn Gln Ala Trp His Leu Val Ala His
                340                 345                 350

Glu Cys Pro Asn Tyr Phe Arg
        355

<210> SEQ ID NO 13
<211> LENGTH: 1020
<212> TYPE: DNA
<213> ORGANISM: Homo sapiens

<400> SEQUENCE: 13

| | | | | | |
|---|---|---|---|---|---|
| atgtggcagc | tctgggcctc | cctctgctgc | ctgctggtgt | tggccaatgc | ccggagcagg | 60 |
| ccctctttcc | atcccctgtc | ggatgagctg | gtcaactatg | tcaacaaacg | gaataccacg | 120 |
| tggcaggccg | ggcacaactt | ctacaacgtg | gacatgagct | acttgaagag | gctatgtggt | 180 |
| accttcctgg | gtgggcccaa | gccaccccag | agagttatgt | ttaccgagga | cctgaagctg | 240 |
| cctgcaagct | tcgatgcacg | ggaacaatgg | ccacagtgtc | ccaccatcaa | agagatcaga | 300 |
| gaccagggct | cctgtggctc | tgctgggcc | ttcggggctg | tggaagccat | ctctgaccgg | 360 |
| atctgcatcc | acaccaatgc | gcacgtcagc | gtggaggtgt | cggcggagga | cctgctcaca | 420 |
| tgctgtggca | gcatgtgtgg | ggacggctgt | aatggtggct | atcctgctga | agcttggaac | 480 |
| ttctggacaa | gaaaaggcct | ggtttctggt | ggcctctatg | aatcccatgt | agggtgcaga | 540 |
| ccgtactcca | tccctccctg | tgagcaccac | gtcaacggct | cccggccccc | atgcacgggg | 600 |
| gagggagata | cccccaagtg | tagcaagatc | tgtgagcctg | gctacagccc | gacctacaaa | 660 |
| caggacaagc | actacggata | caattcctac | agcgtctcca | atagcgagaa | ggacatcatg | 720 |
| gccgagatct | acaaaaacgg | ccccgtggag | ggagctttct | ctgtgtattc | ggacttcctg | 780 |
| ctctacaagt | caggagtgta | ccaacacgtc | accggagaga | tgatgggtgg | ccatgccatc | 840 |
| cgcatcctgg | gctggggagt | ggagaatggc | acaccctact | ggctggttgc | caactcctgg | 900 |
| aacactgact | ggggtgacaa | tggcttcttt | aaaatactca | gaggacagga | tcactgtgga | 960 |
| atcgaatcag | aagtggtggc | tggaattcca | cgcaccgatc | agtactggga | aagatctaa | 1020 |

<210> SEQ ID NO 14
<211> LENGTH: 339
<212> TYPE: PRT
<213> ORGANISM: Homo sapiens

<400> SEQUENCE: 14

Met Trp Gln Leu Trp Ala Ser Leu Cys Cys Leu Leu Val Leu Ala Asn
1               5                   10                  15

Ala Arg Ser Arg Pro Ser Phe His Pro Leu Ser Asp Glu Leu Val Asn
            20                  25                  30

Tyr Val Asn Lys Arg Asn Thr Thr Trp Gln Ala Gly His Asn Phe Tyr
        35                  40                  45

Asn Val Asp Met Ser Tyr Leu Lys Arg Leu Cys Gly Thr Phe Leu Gly
    50                  55                  60

Gly Pro Lys Pro Pro Gln Arg Val Met Phe Thr Glu Asp Leu Lys Leu
65                  70                  75                  80

Pro Ala Ser Phe Asp Ala Arg Glu Gln Trp Pro Gln Cys Pro Thr Ile
                85                  90                  95

Lys Glu Ile Arg Asp Gln Gly Ser Cys Gly Ser Cys Trp Ala Phe Gly
            100                 105                 110

Ala Val Glu Ala Ile Ser Asp Arg Ile Cys Ile His Thr Asn Ala His

```
                    115                 120                 125
Val Ser Val Glu Val Ser Ala Glu Asp Leu Leu Thr Cys Cys Gly Ser
                130                 135                 140

Met Cys Gly Asp Gly Cys Asn Gly Gly Tyr Pro Ala Glu Ala Trp Asn
145                 150                 155                 160

Phe Trp Thr Arg Lys Gly Leu Val Ser Gly Leu Tyr Glu Ser His
                165                 170                 175

Val Gly Cys Arg Pro Tyr Ser Ile Pro Pro Cys Glu His His Val Asn
                180                 185                 190

Gly Ser Arg Pro Pro Cys Thr Gly Glu Gly Asp Thr Pro Lys Cys Ser
                195                 200                 205

Lys Ile Cys Glu Pro Gly Tyr Ser Pro Thr Tyr Lys Gln Asp Lys His
                210                 215                 220

Tyr Gly Tyr Asn Ser Tyr Ser Val Ser Asn Ser Glu Lys Asp Ile Met
225                 230                 235                 240

Ala Glu Ile Tyr Lys Asn Gly Pro Val Glu Gly Ala Phe Ser Val Tyr
                245                 250                 255

Ser Asp Phe Leu Leu Tyr Lys Ser Gly Val Tyr Gln His Val Thr Gly
                260                 265                 270

Glu Met Met Gly Gly His Ala Ile Arg Ile Leu Gly Trp Gly Val Glu
                275                 280                 285

Asn Gly Thr Pro Tyr Trp Leu Val Ala Asn Ser Trp Asn Thr Asp Trp
                290                 295                 300

Gly Asp Asn Gly Phe Phe Lys Ile Leu Arg Gly Gln Asp His Cys Gly
305                 310                 315                 320

Ile Glu Ser Glu Val Val Ala Gly Ile Pro Arg Thr Asp Gln Tyr Trp
                325                 330                 335

Glu Lys Ile

<210> SEQ ID NO 15
<211> LENGTH: 1965
<212> TYPE: DNA
<213> ORGANISM: Homo sapiens

<400> SEQUENCE: 15
atgaagctct ccctggtggc cgcgatgctg ctgctgctca gcgcggcgcg ggccgaggag    60
gaggacaaga aggaggacgt gggcacggtg gtcggcatcg acctgggac cacctactcc   120 tgcgtcggcg tgttcaagaa cggccgcgtg gagatcatcg ccaacgatca gggcaaccgc   180
atcacgccgt cctatgtcgc cttcactcct gaaggggaac gtctgattgg cgatgccgcc   240
aagaaccagc tcacctccaa ccccgagaac acggtctttg acgccaagcg gctcatcggc   300
cgcacgtgga tgacccgtc tgtgcagcag gacatcaagt tcttgccgtt caaggtggtt   360
gaaaagaaaa ctaaaccata cattcaagtt gatattggag gtgggcaaac aaagacattt   420
gctcctgaag aaatttctgc catggttctc actaaaatga agaaaccgc tgaggcttat   480 ttgggaaaga aggttaccca tgcagttgtt actgtaccag cctattttaa tgatgcccaa   540
cgccaagcaa ccaaagacgc tggaactatt gctggcctaa atgttatgag gatcatcaac   600
gagcctacgg cagctgctat tgcttatggc ctggataaga gggaggggga agaacatc   660 ctggtgtttg acctgggtgg cggaaccttc gatgtgtctc ttctcaccat tgacaatggt   720
gtcttcgaag ttgtgccac taatggagat actcatctgg gtggagaaga ctttgaccag   780
cgtgtcatgg aacacttcat caaactgtac aaaaagaaga cgggcaaaga tgtcaggaaa   840
```

```
gacaatagag ctgtgcagaa actccggcgc gaggtagaaa aggccaaacg ggccctgtct      900
tctcagcatc aagcaagaat tgaaattgag tccttctatg aaggagaaga cttttctgag      960
accctgactc gggccaaatt tgaagagctc aacatggatc tgttccggtc tactatgaag     1020
cccgtccaga aagtgttgga agattctgat ttgaagaagt ctgatattga tgaaattgtt     1080
cttgttggtg gctcgactcg aattccaaag attcagcaac tggttaaaga gttcttcaat     1140
ggcaaggaac catcccgtgg cataaaccca gatgaagctg tagcgtatgg tgctgctgtc     1200
caggctggtg tgctctctgg tgatcaagat acaggtgacc tggtactgct tgatgtatgt     1260
ccccttacac ttggtattga aactgtggga ggtgtcatga ccaaactgat tccaaggaac     1320
acagtggtgc ctaccaagaa gtctcagatc ttttctacag cttctgataa tcaaccaact     1380
gttacaatca aggtctatga aggtgaaaga ccccctgacaa agacaatca tcttctgggt     1440 acatttgatc tgactggaat tcctcctgct cctcgtgggg tcccacagat tgaagtcacc     1500
tttgagatag atgtgaatgg tattcttcga gtgacagctg aagacaaggg tacagggaac     1560
aaaaataaga tcacaatcac caatgaccag aatcgcctga cacctgaaga aatcgaaagg     1620
atggttaatg atgctgagaa gtttgctgag gaagacaaaa agctcaagga gcgcattgat     1680
actagaaatg agttggaaag ctatgcctat tctctaaaga atcagattgg agataaagaa     1740
aagctgggag gtaaactttc ctctgaagat aaggagacca tggaaaaagc tgtagaagaa     1800
aagattgaat ggctgaaaag ccaccaagat gctgacattg aagacttcaa agctaagaag     1860
aaggaactgg aagaaattgt tcaaccaatt atcagcaaac tctatggaag tgcaggccct     1920
cccccaactg gtgaagagga tacagcagaa aaagatgagt tgtag                     1965
```

<210> SEQ ID NO 16
<211> LENGTH: 654
<212> TYPE: PRT
<213> ORGANISM: Homo sapiens

<400> SEQUENCE: 16

Met Lys Leu Ser Leu Val Ala Ala Met Leu Leu Leu Leu Ser Ala Ala
1               5                   10                  15

Arg Ala Glu Glu Glu Asp Lys Lys Glu Asp Val Gly Thr Val Val Gly
                20                  25                  30

Ile Asp Leu Gly Thr Thr Tyr Ser Cys Val Gly Val Phe Lys Asn Gly
            35                  40                  45

Arg Val Glu Ile Ile Ala Asn Asp Gln Gly Asn Arg Ile Thr Pro Ser
        50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Glu Lys Lys Thr Lys Pro Tyr Ile
        115                 120                 125

Gln Val Asp Ile Gly Gly Gly Gln Thr Lys Thr Phe Ala Pro Glu Glu
    130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

```
Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
        195                 200                 205

Tyr Gly Leu Asp Lys Arg Glu Gly Glu Lys Asn Ile Leu Val Phe Asp
        210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
            245                 250                 255

Asp Phe Asp Gln Arg Val Met Glu His Phe Ile Lys Leu Tyr Lys Lys
            260                 265                 270

Lys Thr Gly Lys Asp Val Arg Lys Asp Asn Arg Ala Val Gln Lys Leu
        275                 280                 285

Arg Arg Glu Val Glu Lys Ala Lys Arg Ala Leu Ser Ser Gln His Gln
290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
            325                 330                 335

Ser Thr Met Lys Pro Val Gln Lys Val Leu Glu Asp Ser Asp Leu Lys
            340                 345                 350

Lys Ser Asp Ile Asp Glu Ile Val Leu Val Gly Gly Ser Thr Arg Ile
        355                 360                 365

Pro Lys Ile Gln Gln Leu Val Lys Glu Phe Phe Asn Gly Lys Glu Pro
370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
            405                 410                 415

Leu Asp Val Cys Pro Leu Thr Leu Gly Ile Glu Thr Val Gly Gly Val
            420                 425                 430

Met Thr Lys Leu Ile Pro Arg Asn Thr Val Val Pro Thr Lys Lys Ser
        435                 440                 445

Gln Ile Phe Ser Thr Ala Ser Asp Asn Gln Pro Thr Val Thr Ile Lys
        450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
            485                 490                 495

Ile Glu Val Thr Phe Glu Ile Asp Val Asn Gly Ile Leu Arg Val Thr
            500                 505                 510

Ala Glu Asp Lys Gly Thr Gly Asn Lys Asn Lys Ile Thr Ile Thr Asn
        515                 520                 525

Asp Gln Asn Arg Leu Thr Pro Glu Glu Ile Glu Arg Met Val Asn Asp
530                 535                 540

Ala Glu Lys Phe Ala Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
            565                 570                 575

Gly Asp Lys Glu Lys Leu Gly Gly Lys Leu Ser Ser Glu Asp Lys Glu
            580                 585                 590

Thr Met Glu Lys Ala Val Glu Glu Lys Ile Glu Trp Leu Glu Ser His
```

```
                    595                 600                 605
Gln Asp Ala Asp Ile Glu Asp Phe Lys Ala Lys Lys Lys Glu Leu Glu
                610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650
```

<210> SEQ ID NO 17
<211> LENGTH: 666
<212> TYPE: DNA
<213> ORGANISM: Homo sapiens

<400> SEQUENCE: 17

```
atgactacac agttaagggt cgtccatctg cttcccttc tcctagcctg ctttgtgcaa    60
acaagtccca gcaggagaa gatgaagatg gattgccaca agacgagaa aggcaccatc   120
tatgactatg aggccatcgc acttaataag aatgaatatg tttccttcaa gcagtatgtg   180
ggcaagcaca tcctcttcgt caacgtggcc acctactgtg gtctgacagc gcaatatcct   240
gaactaaatg cactccagga ggagctgaag ccctatggtc tagttgtgtt gggctttccc   300
tgcaaccaat ttggaaagca agaaccagga gataacaaag agattcttcc tgggctcaag   360
tatgtccgtc caggggggagg atttgtacct agtttccagc tttttgagaa aggggatgtg   420
aatggtgaaa agaacagaa agtcttcagt ttcttgaagc actcctgtcc tcatccctct   480
gagattttgg gcacattcaa atctatatcc tgggaccctg taaaggtcca tgacatccgt   540
tggaactttg aaaagttcct ggtggggcct gatggaatcc ctgtcatgcg ctggtcccac   600
cgggctacgg tcagctcagt caagacagac atcctggcgt acttgaagca attcaaaacc   660
aaatag                                                              666
```

<210> SEQ ID NO 18
<211> LENGTH: 221
<212> TYPE: PRT
<213> ORGANISM: Homo sapiens

<400> SEQUENCE: 18

```
Met Thr Thr Gln Leu Arg Val Val His Leu Leu Pro Leu Leu Leu Ala
1               5                   10                  15

Cys Phe Val Gln Thr Ser Pro Lys Gln Glu Lys Met Lys Met Asp Cys
                20                  25                  30

His Lys Asp Glu Lys Gly Thr Ile Tyr Asp Tyr Glu Ala Ile Ala Leu
            35                  40                  45

Asn Lys Asn Glu Tyr Val Ser Phe Lys Gln Tyr Val Gly Lys His Ile
        50                  55                  60

Leu Phe Val Asn Val Ala Thr Tyr Cys Gly Leu Thr Ala Gln Tyr Pro
65                  70                  75                  80

Glu Leu Asn Ala Leu Gln Glu Glu Leu Lys Pro Tyr Gly Leu Val Val
                85                  90                  95

Leu Gly Phe Pro Cys Asn Gln Phe Gly Lys Gln Glu Pro Gly Asp Asn
            100                 105                 110

Lys Glu Ile Leu Pro Gly Leu Lys Tyr Val Arg Pro Gly Gly Gly Phe
        115                 120                 125

Val Pro Ser Phe Gln Leu Phe Glu Lys Gly Asp Val Asn Gly Glu Lys
    130                 135                 140

Glu Gln Lys Val Phe Ser Phe Leu Lys His Ser Cys Pro His Pro Ser
```

| | | 145 | | | 150 | | | | 155 | | | | 160 | |
|---|---|---|---|---|---|---|---|---|---|---|---|---|---|---|

Glu Ile Leu Gly Thr Phe Lys Ser Ile Ser Trp Asp Pro Val Lys Val
              165            170                175

His Asp Ile Arg Trp Asn Phe Glu Lys Phe Leu Val Gly Pro Asp Gly
              180                185            190

Ile Pro Val Met Arg Trp Ser His Arg Ala Thr Val Ser Ser Val Lys
              195                200            205

Thr Asp Ile Leu Ala Tyr Leu Lys Gln Phe Lys Thr Lys
              210                215            220

<210> SEQ ID NO 19
<211> LENGTH: 1815
<212> TYPE: DNA
<213> ORGANISM: Homo sapiens

<400> SEQUENCE: 19

```
atggcagggg acgtggaagg attctgttcc tccatccacg acaccagtgt ctctgctggg     60
ttcagagcac tgtatgagga gggattgctt cttgatgtca ctctggttat tgaagatcat    120
cagttccagg cccataaagc actcttggcc acccagagtg attacttcag aattatgttt    180
actgcagaca tgagggaacg agatcaggac aaaattcatt taaaaggtct aacagctacc    240
ggtttcagcc atgtcctgca atttatgtac tatggaacta tagagctgag tatgaatacc    300
gttcatgaga ttcttcaggc tgccatgtat gttcaactta gaagtggt gaagttctgc    360
tgctcttttc tcttagcgaa gatctgccta gaaaattgtg cagaaattat gagactctta    420
gatgatttcg gcgtaaacat cgagggagtc agggagaagt tagacacctt ctgctagac    480
aactttgtgc cactcatgtc taggcctgac tttctgtcct atctgagctt gagaagctc    540
atgtcttact tggataatga tcatctgagc aggttcccag atatagagct gtacgaggct    600
gtgcagtctt ggctgcggca tgatagaaga cgctggagac ataccgatac catcattcag    660
aatatccggt tttgcttgat gaccccaacc agcgttttgt agaaggttaa gacatcagaa    720
ttttatagat actcccgaca gctccgttac gaagttgacc aagcattgaa ttactttcag    780
aatgttcacc agcagccttt gttggatatg aagtcaagcc gcatccgttc tgcaaaaccg    840
caaactacag tatttcgagg aatgattgga catagcatgg ttaacagtaa atacttctc    900
ttaaagaaac caagagtctg gtgggagcta gaaggcccac aagtacctct gcgacctgac    960
tgccttgcta tcgtcaataa ttttgtgttc ctgttaggcg gggaagagct gggcccggat   1020
ggtgaattcc atgcttcttc caaagtattc aggtatgacc cgagacagaa ctcctggctg   1080
cagatggcag atatgtctgt accacgctct gaatttgctg taggtgttat tgggaagttt   1140
atttacgccg tagcaggcag aaccagagat gagactttct attcaactga gagatatgac   1200
atcaccaacg ataaatggga atttgtggat cctatccag ttaacaaata tggacatgag   1260
gggacagtgc tcaataacaa attgtttatc accggtggaa tcacctcatc ttccacctcc   1320
aagcaagtgt gcgtgtttga ccccagcaaa gaagggacca taacaacg gaccaggaga   1380
actcaagtgg ttaccaactg ttgggagaat aagagcaaga tgaattacgc gagatgcttt   1440
cacaagatga tttcttacaa tggcaagctt tatgtcttcg gtggtgtctg tgtgatcttg   1500
agggcctctt tcgaatctca gggatgccct tctacagaag tatacaaccc agagactgat   1560
cagtggacca tcttggcatc catgccgatt ggtagaagtg ccatggtgt gactgtgctg   1620
gacaaacaaa taatgttct tggaggcctt tgttataatg tcattacag cgattccatc   1680
ctcacttttg atccggatga aaacaagtgg aaggaagatg agtaccctcg gatgcctgc   1740
```

-continued

```
aagctggatg gtttacaagt atgcaacctg catttteegg actatgtact ggatgaggte    1800 aggcgttgca actaa                                                     1815
```

<210> SEQ ID NO 20
<211> LENGTH: 604
<212> TYPE: PRT
<213> ORGANISM: Homo sapiens

<400> SEQUENCE: 20

| Met | Ala | Gly | Asp | Val | Glu | Gly | Phe | Cys | Ser | Ile | His | Asp | Thr | Ser |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Val Ser Ala Gly Phe Arg Ala Leu Tyr Glu Glu Gly Leu Leu Leu Asp
            20                  25                  30

Val Thr Leu Val Ile Glu Asp His Gln Phe Gln Ala His Lys Ala Leu
        35                  40                  45

Leu Ala Thr Gln Ser Asp Tyr Phe Arg Ile Met Phe Thr Ala Asp Met
    50                  55                  60

Arg Glu Arg Asp Gln Asp Lys Ile His Leu Lys Gly Leu Thr Ala Thr
65                  70                  75                  80

Gly Phe Ser His Val Leu Gln Phe Met Tyr Tyr Gly Thr Ile Glu Leu
                85                  90                  95

Ser Met Asn Thr Val His Glu Ile Leu Gln Ala Ala Met Tyr Val Gln
            100                 105                 110

Leu Ile Glu Val Val Lys Phe Cys Cys Ser Phe Leu Leu Ala Lys Ile
        115                 120                 125

Cys Leu Glu Asn Cys Ala Glu Ile Met Arg Leu Leu Asp Asp Phe Gly
    130                 135                 140

Val Asn Ile Glu Gly Val Arg Glu Lys Leu Asp Thr Phe Leu Leu Asp
145                 150                 155                 160

Asn Phe Val Pro Leu Met Ser Arg Pro Asp Phe Leu Ser Tyr Leu Ser
                165                 170                 175

Phe Glu Lys Leu Met Ser Tyr Leu Asp Asn Asp His Leu Ser Arg Phe
            180                 185                 190

Pro Glu Ile Glu Leu Tyr Glu Ala Val Gln Ser Trp Leu Arg His Asp
        195                 200                 205

Arg Arg Arg Trp Arg His Thr Asp Thr Ile Ile Gln Asn Ile Arg Phe
    210                 215                 220

Cys Leu Met Thr Pro Thr Ser Val Phe Glu Lys Val Lys Thr Ser Glu
225                 230                 235                 240

Phe Tyr Arg Tyr Ser Arg Gln Leu Arg Tyr Glu Val Asp Gln Ala Leu
                245                 250                 255

Asn Tyr Phe Gln Asn Val His Gln Gln Pro Leu Leu Asp Met Lys Ser
            260                 265                 270

Ser Arg Ile Arg Ser Ala Lys Pro Gln Thr Thr Val Phe Arg Gly Met
        275                 280                 285

Ile Gly His Ser Met Val Asn Ser Lys Ile Leu Leu Lys Lys Pro
    290                 295                 300

Arg Val Trp Trp Glu Leu Glu Gly Pro Gln Val Pro Leu Arg Pro Asp
305                 310                 315                 320

Cys Leu Ala Ile Val Asn Asn Phe Val Phe Leu Leu Gly Gly Glu Glu
                325                 330                 335

Leu Gly Pro Asp Gly Glu Phe His Ala Ser Ser Lys Val Phe Arg Tyr
            340                 345                 350

```
Asp Pro Arg Gln Asn Ser Trp Leu Gln Met Ala Asp Met Ser Val Pro
            355                 360                 365

Arg Ser Glu Phe Ala Val Gly Val Ile Gly Lys Phe Ile Tyr Ala Val
        370                 375                 380

Ala Gly Arg Thr Arg Asp Glu Thr Phe Tyr Ser Thr Glu Arg Tyr Asp
385                 390                 395                 400

Ile Thr Asn Asp Lys Trp Glu Phe Val Asp Pro Tyr Pro Val Asn Lys
                405                 410                 415

Tyr Gly His Glu Gly Thr Val Leu Asn Asn Lys Leu Phe Ile Thr Gly
            420                 425                 430

Gly Ile Thr Ser Ser Ser Thr Ser Lys Gln Val Cys Val Phe Asp Pro
        435                 440                 445

Ser Lys Glu Gly Thr Ile Glu Gln Arg Thr Arg Thr Gln Val Val
450                 455                 460

Thr Asn Cys Trp Glu Asn Lys Ser Lys Met Asn Tyr Ala Arg Cys Phe
465                 470                 475                 480

His Lys Met Ile Ser Tyr Asn Gly Lys Leu Tyr Val Phe Gly Gly Val
                485                 490                 495

Cys Val Ile Leu Arg Ala Ser Phe Glu Ser Gln Gly Cys Pro Ser Thr
            500                 505                 510

Glu Val Tyr Asn Pro Glu Thr Asp Gln Trp Thr Ile Leu Ala Ser Met
        515                 520                 525

Pro Ile Gly Arg Ser Gly His Gly Val Thr Val Leu Asp Lys Gln Ile
        530                 535                 540

Met Val Leu Gly Gly Leu Cys Tyr Asn Gly His Tyr Ser Asp Ser Ile
545                 550                 555                 560

Leu Thr Phe Asp Pro Asp Glu Asn Lys Trp Lys Glu Asp Glu Tyr Pro
                565                 570                 575

Arg Met Pro Cys Lys Leu Asp Gly Leu Gln Val Cys Asn Leu His Phe
            580                 585                 590

Pro Asp Tyr Val Leu Asp Glu Val Arg Arg Cys Asn
        595                 600

<210> SEQ ID NO 21
<211> LENGTH: 1926
<212> TYPE: DNA
<213> ORGANISM: Homo sapiens

<400> SEQUENCE: 21
atggctactg ccaagggaat cgccataggc atcgacctgg caccaccta ctcctgtgtg      60 ggggtgttcc agcacggcaa ggtggagatc atcgccaacg accagggcaa ccgcaccacc     120
cccagctacg tggccttcac agacaccgag cggctcattg gggatgcggc caagaaccag     180
gtagcaatga atccccagaa cactgttttt gatgctaaac gtctgatcgg caggaaattt     240
aatgatcctg ttgtacaagc agatatgaaa ctttggcctt tcaagtgat taatgaagga     300 ggcaagccca agtccttgt gtcctacaaa ggggagaata agctttcta ccctgaggaa     360 atctcttcga tggtattgac taagttgaag gagactgctg aggcctttt gggccaccct      420 gtcaccaatg cagtgattac cgtgccagcc tatttcaatg actctcaacg tcaggctact      480
aaggatgcag gtgtgattgc tggacttaat gtgctaagaa tcatcaatga gcccacggct      540
gctgccattg cctatggttt agataaagga ggtcaaggag aacgacatgt cctgattttt      600
gatctgggtg gaggcacatt tgatgtgtca attctgacca gatgatgg gattttttgag      660 gtaaaggcca ctgctgggga cactcacctg ggtggggagg actttgacaa caggcttgtg     720
```

-continued

```
agccacttcg tggaggagtt caagaggaaa cacaaaaagg acatcagcca gaacaagcga     780
gccgtgaggc ggctgcgcac cgcctgcgag agggccaaga ggaccctgtc gtccagcacc     840
caggccaacc tagaaattga ttcactttat gaaggcattg acttctatac atccatcacc     900
agagctcgat ttgaagagtt gtgtgcagac ctgtttaggg gtaccctgga gcctgtagaa     960
aaagcgcttc gggatgccaa gatggataag gctaaaatcc atgacattgt tttagtaggg    1020
ggctccaccc gcatccccaa ggtgcagcgg ctgcttcagg actacttcaa tggacgtgat    1080
ctcaacaaga gcatcaaccc tgatgaggcc gtagcatatg gggctgcggt acaagcagcc    1140
atcctgatgg gggacaagtc tgagaaggta caggacctgc tgctgctgga cgtggctccc    1200
ctgtccctgg ggctggagac ggctgggggc gtgatgactg ccctgataaa gcgcaactcc    1260
accatcccca ccaagcagac acagattttc accacctact ctgacaacca acccggggtg    1320
ctgatccagg tgtatgaggg cgagagggcc atgacaaagg acaacaacct gctggggcgg    1380
tttgacctga ctggaatccc tccagcaccc aggggagttc ctcagatcga ggtgacgttt    1440
gacattgatg ccaatggtat tctcaatgtc acagccacgg acaagagcac cggcaaggtg    1500
aacaagatca ccatcaccaa tgacaagggc cgcctgagca aggaggagat tgagcgcatg    1560
gttctggatg ctgagaaata taagctgaa gatgaggtcc agagggagaa aattgctgca    1620
aagaatgcct tagaatccta tgcttttaac atgaagagtg ttgtgagtga tgaaggtttg    1680
aagggcaaga ttagtgagtc tgataaaaat aaaatattgg ataaatgcaa cgagctcctt    1740
tcgtggctgg aggtcaatca actggcgagag aaagatgagt ttgatcataa agagaaggaa    1800
ttggagcaga tgtgtaaccc tatcatcaca aaactctacc aaggaggatg cactgggcct    1860
gcctgcggaa cagggtatgt gcctggaagg cctgccacag gccccacaat tgaagaagta    1920
gattaa                                                               1926
```

<210> SEQ ID NO 22
<211> LENGTH: 641
<212> TYPE: PRT
<213> ORGANISM: Homo sapiens

<400> SEQUENCE: 22

| Met | Ala | Thr | Ala | Lys | Gly | Ile | Ala | Ile | Gly | Ile | Asp | Leu | Gly | Thr | Thr |
|---|---|---|---|---|---|---|---|---|---|---|---|---|---|---|---|
| 1 | | | | 5 | | | | | 10 | | | | | 15 | |

| Tyr | Ser | Cys | Val | Gly | Val | Phe | Gln | His | Gly | Lys | Val | Glu | Ile | Ile | Ala |
| | | | 20 | | | | | 25 | | | | | 30 | | |

| Asn | Asp | Gln | Gly | Asn | Arg | Thr | Thr | Pro | Ser | Tyr | Val | Ala | Phe | Thr | Asp |
| | | | 35 | | | | 40 | | | | | 45 | | | |

| Thr | Glu | Arg | Leu | Ile | Gly | Asp | Ala | Ala | Lys | Asn | Gln | Val | Ala | Met | Asn |
| | 50 | | | | | 55 | | | | | 60 | | | | |

| Pro | Gln | Asn | Thr | Val | Phe | Asp | Ala | Lys | Arg | Leu | Ile | Gly | Arg | Lys | Phe |
| 65 | | | | | 70 | | | | | 75 | | | | | 80 |

| Asn | Asp | Pro | Val | Val | Gln | Ala | Asp | Met | Lys | Leu | Trp | Pro | Phe | Gln | Val |
| | | | | 85 | | | | | 90 | | | | | 95 | |

| Ile | Asn | Glu | Gly | Gly | Lys | Pro | Lys | Val | Leu | Val | Ser | Tyr | Lys | Gly | Glu |
| | | | | 100 | | | | | 105 | | | | | 110 | |

| Asn | Lys | Ala | Phe | Tyr | Pro | Glu | Glu | Ile | Ser | Ser | Met | Val | Leu | Thr | Lys |
| | | | 115 | | | | | 120 | | | | | 125 | | |

| Leu | Lys | Glu | Thr | Ala | Glu | Ala | Phe | Leu | Gly | His | Pro | Val | Thr | Asn | Ala |
| | 130 | | | | | 135 | | | | | 140 | | | | |

Val Ile Thr Val Pro Ala Tyr Phe Asn Asp Ser Gln Arg Gln Ala Thr

```
            145                 150                 155                 160
Lys Asp Ala Gly Val Ile Ala Gly Leu Asn Val Leu Arg Ile Ile Asn
                    165                 170                 175
Glu Pro Thr Ala Ala Ala Ile Ala Tyr Gly Leu Asp Lys Gly Gly Gln
                    180                 185                 190
Gly Glu Arg His Val Leu Ile Phe Asp Leu Gly Gly Gly Thr Phe Asp
                    195                 200                 205
Val Ser Ile Leu Thr Ile Asp Asp Gly Ile Phe Glu Val Lys Ala Thr
                    210                 215                 220
Ala Gly Asp Thr His Leu Gly Gly Glu Asp Phe Asp Asn Arg Leu Val
225                 230                 235                 240
Ser His Phe Val Glu Glu Phe Lys Arg Lys His Lys Lys Asp Ile Ser
                    245                 250                 255
Gln Asn Lys Arg Ala Val Arg Arg Leu Arg Thr Ala Cys Glu Arg Ala
                    260                 265                 270
Lys Arg Thr Leu Ser Ser Ser Thr Gln Ala Asn Leu Glu Ile Asp Ser
                    275                 280                 285
Leu Tyr Glu Gly Ile Asp Phe Tyr Thr Ser Ile Thr Arg Ala Arg Phe
                    290                 295                 300
Glu Glu Leu Cys Ala Asp Leu Phe Arg Gly Thr Leu Glu Pro Val Glu
305                 310                 315                 320
Lys Ala Leu Arg Asp Ala Lys Met Asp Lys Ala Lys Ile His Asp Ile
                    325                 330                 335
Val Leu Val Gly Gly Ser Thr Arg Ile Pro Lys Val Gln Arg Leu Leu
                    340                 345                 350
Gln Asp Tyr Phe Asn Gly Arg Asp Leu Asn Lys Ser Ile Asn Pro Asp
                    355                 360                 365
Glu Ala Val Ala Tyr Gly Ala Ala Val Gln Ala Ala Ile Leu Met Gly
                    370                 375                 380
Asp Lys Ser Glu Lys Val Gln Asp Leu Leu Leu Leu Asp Val Ala Pro
385                 390                 395                 400
Leu Ser Leu Gly Leu Glu Thr Ala Gly Gly Val Met Thr Ala Leu Ile
                    405                 410                 415
Lys Arg Asn Ser Thr Ile Pro Thr Lys Gln Thr Gln Ile Phe Thr Thr
                    420                 425                 430
Tyr Ser Asp Asn Gln Pro Gly Val Leu Ile Gln Val Tyr Glu Gly Glu
                    435                 440                 445
Arg Ala Met Thr Lys Asp Asn Asn Leu Leu Gly Arg Phe Asp Leu Thr
                    450                 455                 460
Gly Ile Pro Pro Ala Pro Arg Gly Val Pro Gln Ile Glu Val Thr Phe
465                 470                 475                 480
Asp Ile Asp Ala Asn Gly Ile Leu Asn Val Thr Ala Thr Asp Lys Ser
                    485                 490                 495
Thr Gly Lys Val Asn Lys Ile Thr Ile Thr Asn Asp Lys Gly Arg Leu
                    500                 505                 510
Ser Lys Glu Glu Ile Glu Arg Met Val Leu Asp Ala Glu Lys Tyr Lys
                    515                 520                 525
Ala Glu Asp Glu Val Gln Arg Glu Lys Ile Ala Ala Lys Asn Ala Leu
                    530                 535                 540
Glu Ser Tyr Ala Phe Asn Met Lys Ser Val Val Ser Asp Glu Gly Leu
545                 550                 555                 560
Lys Gly Lys Ile Ser Glu Ser Asp Lys Asn Lys Ile Leu Asp Lys Cys
                    565                 570                 575
```

```
Asn Glu Leu Leu Ser Trp Leu Glu Val Asn Gln Leu Ala Glu Lys Asp
                580                 585                 590

Glu Phe Asp His Lys Arg Lys Glu Leu Glu Gln Met Cys Asn Pro Ile
            595                 600                 605

Ile Thr Lys Leu Tyr Gln Gly Gly Cys Thr Gly Pro Ala Cys Gly Thr
        610                 615                 620

Gly Tyr Val Pro Gly Arg Pro Ala Thr Gly Pro Thr Ile Glu Glu Val
625                 630                 635                 640

Asp

<210> SEQ ID NO 23
<211> LENGTH: 2265
<212> TYPE: DNA
<213> ORGANISM: Homo sapiens

<400> SEQUENCE: 23
```

| | | | | | |
|---|---|---|---|---|---|
| atgcttcccg | ggtgtatatt | cttgatgatt | ttactcattc | ctcaggttaa | agaaaagttc | 60 |
| atccttggag | tagagggtca | caactggtt | cgtcctaaaa | agcttcctct | gatacagaag | 120 |
| cgagatactg | gacacaccca | tgatgatgac | atactgaaaa | cgtatgaaga | agaattgttg | 180 |
| tatgaaataa | aactaaatag | aaaaacctta | gtccttcatc | ttctaagatc | cagggagttc | 240 |
| ctaggctcaa | attacagtga | aacattctac | tccatgaaag | gagaagcgtt | caccaggcat | 300 |
| cctcagatca | tggatcattg | ttttttaccaa | ggatccatag | tacacgaata | tgattcagct | 360 |
| gccagtatca | gtacgtgtaa | tggtctaagg | ggattcttca | gaataaacga | ccaaagatac | 420 |
| ctcattgaac | cagtgaaata | ctcagatgag | ggagaacatt | tggtgttcaa | atataacctg | 480 |
| agggtgccgt | atggtgccaa | ttattcctgt | acagagctta | attttaccag | aaaaactgtt | 540 |
| ccaggggata | atgaatctga | gaagactcc | aaaataaaag | gcatccatga | tgaaaagtat | 600 |
| gttgaattgt | tcattgttgc | tgatgatact | gtgtatcgca | gaaatggtca | tcctcacaat | 660 |
| aaactaagga | accgaatttg | gggaatggtc | aattttgtca | acatgattta | taaaacctta | 720 |
| aacatccatg | tgacgttggt | tggcattgaa | atatggacac | atgaagataa | aatagaacta | 780 |
| tattcaaata | tagaaactac | cttattgcgt | ttttcatttt | ggcaagaaaa | gatccttaaa | 840 |
| acacggaagg | attttgatca | tgttgtatta | ctcagtggga | agtggctcta | ctcacatgtg | 900 |
| caaggaattt | cttatccagg | gggtatgtgc | ctgcccatt | attccaccag | tatcattaag | 960 |
| gatctttac | ctgacacaaa | cataattgca | acagaatgg | cacatcaact | ggggcataac | 1020 |
| cttgggatgc | agcatgacga | gttcccatgc | acctgtcctt | caggaaaatg | cgtgatggac | 1080 |
| agtgatggaa | gcattcctgc | actgaaattc | agtaaatgca | gccaaaacca | ataccaccag | 1140 |
| tacttgaagg | attataagcc | aacatgcatg | ctcaacattc | catttcctta | caattttcat | 1200 |
| gatttccaat | tttgtggaaa | caagaagttg | gatgagggtg | aagagtgtga | ctgtggccct | 1260 |
| gctcaggagt | gtactaatcc | ttgctgtgat | gcacacacat | gtgtactgaa | gccaggatt | 1320 |
| acttgtgcag | aaggagaatg | ctgtgaatct | tgtcagataa | aaaagcagg | gtccatatgc | 1380 |
| agaccggcga | agatgaatg | tgattttcct | gagatgtgca | ctggccactc | gcctgcctgt | 1440 |
| cctaaggacc | agttcagggt | caatggattt | ccttgcaaga | actcagaagg | ctactgtttc | 1500 |
| atggggaaat | gtccaactcg | tgaggatcag | tgctctgaac | tatttgatga | tgaggcaata | 1560 |
| gagagtcatg | atatctgcta | caagatgaat | acaaaaggaa | ataaatttgg | atactgcaaa | 1620 |
| aacaaggaaa | acagatttct | tcccctgtgag | gagaaagatg | tcagatgtgg | aaagatctac | 1680 |

```
tgcactggag gggagctttc ctctctcctt ggagaagaca agacttatca ccttaaggat      1740
ccccagaaga atgctactgt caaatgcaaa actattttt tataccatga ttctacagac       1800
attggcctgg tggcgtcagg aacaaaatgt ggagagggaa tggtgtgcaa caatggtgaa      1860
tgtctaaaca tggaaaaggt ctatatctca accaattgcc cctctcagtg caatgaaaat      1920
cctgtggatg ccacggact ccagtgccac tgtgaggaag acaggcacc tgtagcctgt        1980 gaagaaacct tacatgttac caatatcacc atcttggttg ttgtgcttgt cctggttatt      2040
gtcggtatcg gagttcttat actattagtt cgttaccgaa aatgtatcaa gttgaagcaa      2100
gttcagagcc cacctacaga aaccctggga gtggagaaca aaggatactt tggtgatgag      2160
cagcagataa ggactgagcc aatcctgcca gaaattcatt tcctaaataa acctgcaagt     2220
aaagattcaa gaggaatcgc agatcccaat caaagtgcca agtga                      2265
```

<210> SEQ ID NO 24
<211> LENGTH: 754
<212> TYPE: PRT
<213> ORGANISM: Homo sapiens

<400> SEQUENCE: 24

```
Met Leu Pro Gly Cys Ile Phe Leu Met Ile Leu Leu Ile Pro Gln Val
1               5                   10                  15

Lys Glu Lys Phe Ile Leu Gly Val Glu Gly Gln Gln Leu Val Arg Pro
                20                  25                  30

Lys Lys Leu Pro Leu Ile Gln Lys Arg Asp Thr Gly His Thr His Asp
            35                  40                  45

Asp Asp Ile Leu Lys Thr Tyr Glu Glu Leu Leu Tyr Glu Ile Lys
    50                  55                  60

Leu Asn Arg Lys Thr Leu Val Leu His Leu Leu Arg Ser Arg Glu Phe
65                  70                  75                  80

Leu Gly Ser Asn Tyr Ser Glu Thr Phe Tyr Ser Met Lys Gly Glu Ala
                85                  90                  95

Phe Thr Arg His Pro Gln Ile Met Asp His Cys Phe Tyr Gln Gly Ser
                100                 105                 110

Ile Val His Glu Tyr Asp Ser Ala Ala Ser Ile Ser Thr Cys Asn Gly
            115                 120                 125

Leu Arg Gly Phe Phe Arg Ile Asn Asp Gln Arg Tyr Leu Ile Glu Pro
    130                 135                 140

Val Lys Tyr Ser Asp Glu Gly Glu His Leu Val Phe Lys Tyr Asn Leu
145                 150                 155                 160

Arg Val Pro Tyr Gly Ala Asn Tyr Ser Cys Thr Glu Leu Asn Phe Thr
                165                 170                 175

Arg Lys Thr Val Pro Gly Asp Asn Glu Ser Glu Asp Ser Lys Ile
                180                 185                 190

Lys Gly Ile His Asp Glu Lys Tyr Val Glu Leu Phe Ile Val Ala Asp
            195                 200                 205

Asp Thr Val Tyr Arg Arg Asn Gly His Pro His Asn Lys Leu Arg Asn
    210                 215                 220

Arg Ile Trp Gly Met Val Asn Phe Val Asn Met Ile Tyr Lys Thr Leu
225                 230                 235                 240

Asn Ile His Val Thr Leu Val Gly Ile Glu Ile Trp Thr His Glu Asp
                245                 250                 255

Lys Ile Glu Leu Tyr Ser Asn Ile Glu Thr Thr Leu Leu Arg Phe Ser
                260                 265                 270
```

-continued

Phe Trp Gln Glu Lys Ile Leu Lys Thr Arg Lys Asp Phe Asp His Val
            275                 280                 285
Val Leu Leu Ser Gly Lys Trp Leu Tyr Ser His Val Gln Gly Ile Ser
290                 295                 300
Tyr Pro Gly Gly Met Cys Leu Pro Tyr Ser Thr Ser Ile Ile Lys
305                 310                 315                 320
Asp Leu Leu Pro Asp Thr Asn Ile Ile Ala Asn Arg Met Ala His Gln
                325                 330                 335
Leu Gly His Asn Leu Gly Met Gln His Asp Glu Phe Pro Cys Thr Cys
            340                 345                 350
Pro Ser Gly Lys Cys Val Met Asp Ser Asp Gly Ser Ile Pro Ala Leu
            355                 360                 365
Lys Phe Ser Lys Cys Ser Gln Asn Gln Tyr His Gln Tyr Leu Lys Asp
370                 375                 380
Tyr Lys Pro Thr Cys Met Leu Asn Ile Pro Phe Pro Tyr Asn Phe His
385                 390                 395                 400
Asp Phe Gln Phe Cys Gly Asn Lys Lys Leu Asp Glu Gly Glu Glu Cys
                405                 410                 415
Asp Cys Gly Pro Ala Gln Glu Cys Thr Asn Pro Cys Cys Asp Ala His
            420                 425                 430
Thr Cys Val Leu Lys Pro Gly Phe Thr Cys Ala Glu Gly Glu Cys Cys
            435                 440                 445
Glu Ser Cys Gln Ile Lys Lys Ala Gly Ser Ile Cys Arg Pro Ala Lys
            450                 455                 460
Asp Glu Cys Asp Phe Pro Glu Met Cys Thr Gly His Ser Pro Ala Cys
465                 470                 475                 480
Pro Lys Asp Gln Phe Arg Val Asn Gly Phe Pro Cys Lys Asn Ser Glu
                485                 490                 495
Gly Tyr Cys Phe Met Gly Lys Cys Pro Thr Arg Glu Asp Gln Cys Ser
            500                 505                 510
Glu Leu Phe Asp Asp Glu Ala Ile Glu Ser His Asp Ile Cys Tyr Lys
            515                 520                 525
Met Asn Thr Lys Gly Asn Lys Phe Gly Tyr Cys Lys Asn Lys Glu Asn
530                 535                 540
Arg Phe Leu Pro Cys Glu Glu Lys Asp Val Arg Cys Gly Lys Ile Tyr
545                 550                 555                 560
Cys Thr Gly Gly Glu Leu Ser Ser Leu Leu Gly Glu Asp Lys Thr Tyr
                565                 570                 575
His Leu Lys Asp Pro Gln Lys Asn Ala Thr Val Lys Cys Lys Thr Ile
            580                 585                 590
Phe Leu Tyr His Asp Ser Thr Asp Ile Gly Leu Val Ala Ser Gly Thr
            595                 600                 605
Lys Cys Gly Glu Gly Met Val Cys Asn Asn Gly Glu Cys Leu Asn Met
610                 615                 620
Glu Lys Val Tyr Ile Ser Thr Asn Cys Pro Ser Gln Cys Asn Glu Asn
625                 630                 635                 640
Pro Val Asp Gly His Gly Leu Gln Cys His Cys Glu Glu Gly Gln Ala
                645                 650                 655
Pro Val Ala Cys Glu Glu Thr Leu His Val Thr Asn Ile Thr Ile Leu
            660                 665                 670
Val Val Val Leu Val Leu Val Ile Gly Ile Gly Val Leu Ile Leu
            675                 680                 685
Leu Val Arg Tyr Arg Lys Cys Ile Lys Leu Lys Gln Val Gln Ser Pro

```
                    690                695                700
Pro Thr Glu Thr Leu Gly Val Glu Asn Lys Gly Tyr Phe Gly Asp Glu
705                     710                715                720

Gln Gln Ile Arg Thr Glu Pro Ile Leu Pro Glu Ile His Phe Leu Asn
                    725                730                735

Lys Pro Ala Ser Lys Asp Ser Arg Gly Ile Ala Asp Pro Asn Gln Ser
                740                745                750

Ala Lys

<210> SEQ ID NO 25
<211> LENGTH: 636
<212> TYPE: DNA
<213> ORGANISM: Homo sapiens

<400> SEQUENCE: 25
atggccaatt cgggcctgca gttgctgggc ttctccatgg ccctgctggg ctgggtgggt      60
ctggtggcct gcaccgccat cccgcagtgg cagatgagct cctatgcggg tgacaacatc     120
atcacggccc aggccatgta caaggggctg tggatggact gcgtcacgca gagcacgggg     180
atgatgagct gcaaaatgta cgactcggtg ctcgccctgt ccgcggcctt gcaggccact     240
cgagccctaa tggtggtctc cctggtgctg ggcttcctgg ccatgtttgt ggccacgatg     300
ggcatgaagt gcacgcgctg tggggagac gacaaagtga agaaggcccg tatagccatg     360
ggtggaggca atttttcat cgtggcaggt cttgccgcct tggtagcttg ctcctggtat     420
ggccatcaga ttgtcacaga cttttataac cctttgatcc ctaccaacat taagtatgag     480
tttggccctg ccatctttat tggctgggca gggtctgccc tagtcatcct gggaggtgca     540
ctgctctcct gttcctgtcc tgggaatgag agcaaggctg ggtaccgtgt accccgctct     600
taccctaagt ccaactcttc caaggagtat gtgtga                                636

<210> SEQ ID NO 26
<211> LENGTH: 211
<212> TYPE: PRT
<213> ORGANISM: Homo sapiens

<400> SEQUENCE: 26

Met Ala Asn Ser Gly Leu Gln Leu Leu Gly Phe Ser Met Ala Leu Leu
1               5                   10                  15

Gly Trp Val Gly Leu Val Ala Cys Thr Ala Ile Pro Gln Trp Gln Met
                20                  25                  30

Ser Ser Tyr Ala Gly Asp Asn Ile Ile Thr Ala Gln Ala Met Tyr Lys
            35                  40                  45

Gly Leu Trp Met Asp Cys Val Thr Gln Ser Thr Gly Met Met Ser Cys
        50                  55                  60

Lys Met Tyr Asp Ser Val Leu Ala Leu Ser Ala Ala Leu Gln Ala Thr
65                  70                  75                  80

Arg Ala Leu Met Val Val Ser Leu Val Leu Gly Phe Leu Ala Met Phe
                85                  90                  95

Val Ala Thr Met Gly Met Lys Cys Thr Arg Cys Gly Gly Asp Asp Lys
                100                 105                 110

Val Lys Lys Ala Arg Ile Ala Met Gly Gly Gly Ile Phe Ile Val
            115                 120                 125

Ala Gly Leu Ala Ala Leu Val Ala Cys Ser Trp Tyr Gly His Gln Ile
        130                 135                 140

Val Thr Asp Phe Tyr Asn Pro Leu Ile Pro Thr Asn Ile Lys Tyr Glu
```

| | 145 | | | 150 | | | 155 | | | 160 | |
|---|---|---|---|---|---|---|---|---|---|---|---|
| Phe | Gly | Pro | Ala | Ile | Phe | Ile | Gly | Trp | Ala | Gly | Ser | Ala | Leu | Val | Ile |
| | | | | 165 | | | | 170 | | | | 175 | | | |

Leu Gly Gly Ala Leu Leu Ser Cys Ser Cys Pro Gly Asn Glu Ser Lys
    180                   185                190

Ala Gly Tyr Arg Val Pro Arg Ser Tyr Pro Lys Ser Asn Ser Ser Lys
      195               200               205

Glu Tyr Val
    210

<210> SEQ ID NO 27
<211> LENGTH: 1692
<212> TYPE: DNA
<213> ORGANISM: Homo sapiens

<400> SEQUENCE: 27

```
atgctgctgc cggcgcccgc gctccgccgc gccctgctgt cccgcccctg gaccggggcc      60
ggcctgcggt ggaagcacac ctcctccctg aaggtggcca cgagcccgt cttagccttc     120
acgcagggca gccctgagcg agatgccctg caaaaggcct tgaaggacct gaagggccgg     180
atggaagcca tcccatgcgt ggtggggat gaggaggtgt ggacgtcgga cgtgcagtac     240
caagtgtcgc ctttaacca tggacataag gtggccaagt tctgttatgc agacaagagc     300
ctgctcaaca aagccattga gctgccctg gctgccgga agagtggga cctgaagcct     360
attgcagacc gggcccagat cttcctgaag gcggcagaca tgctgagtgg gccgcgcagg     420
gctgagatcc tcgccaagac catggtggga cagggtaaga ccgtgatcca gcggagatt     480
gacgctgcag cggaactcat cgacttcttc cggttcaatg ccaagtatgc ggtggagctg     540
gaggggcagc agcccatcag cgtgccccg agcaccaaca gcacggtgta ccggggtctg     600
gagggcttcg tggcggccat ctcgccctt aacttcactg caatcggcgg caacctggcg     660
ggggcaccgg ccctgatggg caacgtggtc ctatggaagc cagtgacac tgccatgctg     720
gccagctatg ctgtctaccg catccttcgg gaggctggcc tgcccccaa catcatccag     780
tttgtgccag ctgatgggcc cctatttggg gacactgtca ccagctcaga gcacctctgt     840
ggcatcaact tcacaggcag tgtgcccacc ttcaaacacc tgtggaagca ggtggcccag     900
aacctggacc ggttccacac cttcccacgc ctggctggag agtgcggcgg aaagaacttc     960
cacttcgtgc accgctcggc cgacgtggag agcgtggtga gcgggaccct ccgctcagcc    1020
ttcgagtacg gtggccagaa gtgttccgcg tgctcgcgtc tctacgtgcc gcactcgctg    1080
tggccgcaga tcaaagggcg gctgctggag agcacagtc ggatcaaagt gggcgaccct    1140
gcagaggatt tgggaccttt cttctctgca gtgattgatg ccaagtcctt tgcccgtatc    1200
aagaagtggc tggagcacgc acgctcctca cccagcctca ccatcctggc cggggggcaag    1260
tgtgatgact ccgtgggcta ctttgtggag ccctgcatcg tggagagcaa ggaccctcag    1320
gagcccatca tgaaggagga gatcttcggg cctgtactgt ctgtgtacgt ctacccggat    1380
gacaagtaca aggagacgct gcagctggtt gacagcacca ccagctatgg cctcacgggg    1440
gcagtgttct cccaggataa ggacgtcgtg caggaggcca caaaggtgct gaggaatgct    1500
gccggcaact tctacatcaa cgacaagtcc actggctcga tagtgggcca gcagcccttt    1560
ggggggccc gagcctctgg aaccaatgac aagccagggg gcccacacta catcctgcgc    1620
tggacgtcgc cgcaggtcat caaggagaca cataagcccc tggggactg gagctacgcg    1680
tacatgcagt ga                                                        1692
```

<210> SEQ ID NO 28
<211> LENGTH: 563
<212> TYPE: PRT
<213> ORGANISM: Homo sapiens

<400> SEQUENCE: 28

Met Leu Leu Pro Ala Pro Ala Leu Arg Arg Ala Leu Ser Arg Pro
1               5                   10                  15

Trp Thr Gly Ala Gly Leu Arg Trp Lys His Thr Ser Ser Leu Lys Val
            20                  25                  30

Ala Asn Glu Pro Val Leu Ala Phe Thr Gln Gly Ser Pro Glu Arg Asp
        35                  40                  45

Ala Leu Gln Lys Ala Leu Lys Asp Leu Lys Gly Arg Met Glu Ala Ile
    50                  55                  60

Pro Cys Val Val Gly Asp Glu Glu Val Trp Thr Ser Asp Val Gln Tyr
65                  70                  75                  80

Gln Val Ser Pro Phe Asn His Gly His Lys Val Ala Lys Phe Cys Tyr
                85                  90                  95

Ala Asp Lys Ser Leu Leu Asn Lys Ala Ile Glu Ala Leu Ala Ala
            100                 105                 110

Arg Lys Glu Trp Asp Leu Lys Pro Ile Ala Asp Arg Ala Gln Ile Phe
        115                 120                 125

Leu Lys Ala Ala Asp Met Leu Ser Gly Pro Arg Arg Ala Glu Ile Leu
    130                 135                 140

Ala Lys Thr Met Val Gly Gln Gly Lys Thr Val Ile Gln Ala Glu Ile
145                 150                 155                 160

Asp Ala Ala Ala Glu Leu Ile Asp Phe Phe Arg Phe Asn Ala Lys Tyr
                165                 170                 175

Ala Val Glu Leu Glu Gly Gln Gln Pro Ile Ser Val Pro Pro Ser Thr
            180                 185                 190

Asn Ser Thr Val Tyr Arg Gly Leu Glu Gly Phe Val Ala Ala Ile Ser
        195                 200                 205

Pro Phe Asn Phe Thr Ala Ile Gly Gly Asn Leu Ala Gly Ala Pro Ala
    210                 215                 220

Leu Met Gly Asn Val Val Leu Trp Lys Pro Ser Asp Thr Ala Met Leu
225                 230                 235                 240

Ala Ser Tyr Ala Val Tyr Arg Ile Leu Arg Glu Ala Gly Leu Pro Pro
                245                 250                 255

Asn Ile Ile Gln Phe Val Pro Ala Asp Gly Pro Leu Phe Gly Asp Thr
            260                 265                 270

Val Thr Ser Ser Glu His Leu Cys Gly Ile Asn Phe Thr Gly Ser Val
        275                 280                 285

Pro Thr Phe Lys His Leu Trp Lys Gln Val Ala Gln Asn Leu Asp Arg
    290                 295                 300

Phe His Thr Phe Pro Arg Leu Ala Gly Glu Cys Gly Gly Lys Asn Phe
305                 310                 315                 320

His Phe Val His Arg Ser Ala Asp Val Glu Ser Val Val Ser Gly Thr
                325                 330                 335

Leu Arg Ser Ala Phe Glu Tyr Gly Gly Gln Lys Cys Ser Ala Cys Ser
            340                 345                 350

Arg Leu Tyr Val Pro His Ser Leu Trp Pro Gln Ile Lys Gly Arg Leu
        355                 360                 365

Leu Glu Glu His Ser Arg Ile Lys Val Gly Asp Pro Ala Glu Asp Phe

Gly Thr Phe Phe Ser Ala Val Ile Asp Ala Lys Ser Phe Ala Arg Ile
370                 375                 380
Lys Lys Trp Leu Glu His Ala Arg Ser Ser Pro Ser Leu Thr Ile Leu
385                 390                 395                 400
Ala Gly Gly Lys Cys Asp Asp Ser Val Gly Tyr Phe Val Glu Pro Cys
        405                 410                 415
Ile Val Glu Ser Lys Asp Pro Gln Glu Pro Ile Met Lys Glu Glu Ile
            420                 425                 430
Phe Gly Pro Val Leu Ser Val Tyr Val Tyr Pro Asp Asp Lys Tyr Lys
                435                 440                 445
Glu Thr Leu Gln Leu Val Asp Ser Thr Thr Ser Tyr Gly Leu Thr Gly
450                 455                 460
Ala Val Phe Ser Gln Asp Lys Asp Val Val Gln Glu Ala Thr Lys Val
465                 470                 475                 480
Leu Arg Asn Ala Ala Gly Asn Phe Tyr Ile Asn Asp Lys Ser Thr Gly
        485                 490                 495
Ser Ile Val Gly Gln Gln Pro Phe Gly Gly Ala Arg Ala Ser Gly Thr
            500                 505                 510
Asn Asp Lys Pro Gly Gly Pro His Tyr Ile Leu Arg Trp Thr Ser Pro
                515                 520                 525
Gln Val Ile Lys Glu Thr His Lys Pro Leu Gly Asp Trp Ser Tyr Ala
530                 535                 540
Tyr Met Gln
545                 550                 555                 560

<210> SEQ ID NO 29
<211> LENGTH: 1554
<212> TYPE: DNA
<213> ORGANISM: Homo sapiens

<400> SEQUENCE: 29

```
atgttgcgcg ctgccgcccg cttcgggccc cgcctgggcc gccgcctctt gtcagccgcc      60
gccacccagg ccgtgcctgc ccccaaccag cagcccgagg tcttctgcaa ccagattttc     120
ataaacaatg aatggcacga tgccgtcagc aggaaaacat tccccaccgt caatccgtcc     180
actggagagg tcatctgtca ggtagctgaa ggggacaagg aagatgtgga caaggcagtg     240
aaggccgccc gggccgcctt ccagctgggc tcaccttggc gccgcatgga cgcatcacac     300
aggggccggc tgctgaaccg cctggccgat ctgatcgagc gggaccggac ctacctggcg     360
gccttggaga ccctggacaa tggcaagccc tatgtcatct cctacctggt ggatttggac     420
atggtcctca atgtctccg gtattatgcc ggctgggctg ataagtacca cgggaaaacc     480
atccccattg acgagactt cttcagctac acacgccatg aacctgtggg ggtgtgcggg     540
cagatcattc cgtggaattt cccgctcctg atgcaagcat ggaagctggg cccagccttg     600
gcaactggaa acgtggttgt gatgaaggta gctgagcaga caccctcac cgccctctat     660
gtggccaacc tgatcaagga ggctggcttt ccccctggtg tggtcaacat tgtgcctgga     720
tttggcccca cggctgggc cgccattgcc tcccatgagg atgtggacaa gtggcattc     780
acaggctcca ctgagattgg ccgcgtaatc caggttgctg ctgggagcag caacctcaag     840
agagtgacct ggagctgggg gggaagagc cccaacatca tcatgtcaga tgccgatatg     900
gattgggccg tggaacaggc ccacttcgcc ctgttcttca accagggcca gtgctgctgt     960
gccggctccc ggaccttcgt gcaggaggac atctatgatg agtttgtgga gcggagcgtt    1020
```

```
gcccgggcca agtctcgggt ggtcgggaac cccttttgata gcaagaccga gcaggggccg   1080
caggtggatg aaactcagtt taagaagatc ctcggctaca tcaacacggg aagcaagag    1140 ggggcgaagc tgctgtgtgg tgggggcatt gctgctgacc gtggttactt catccagccc   1200
actgtgtttg agatgtgcca ggatggcatg accatcgcca aggaggagat cttcgggcca   1260
gtgatgcaga tcctgaagtt caagaccata gaggaggttg ttgggagagc aacaattcc    1320 acgtacgggc tggccgcagc tgtcttcaca aaggatttgg acaaggccaa ttacctgtcc   1380
caggccctcc aggcgggcac tgtgtgggtc aactgctatg atgtgtttgg agcccagtca   1440 cccttttggtg gctacaagat gtcggggagt ggccgggagt tgggcgagta cgggctgcag   1500
gcatacactg aagtgaaaac tgtcacagtc aaagtgcctc agaagaactc ataa          1554
```

<210> SEQ ID NO 30
<211> LENGTH: 517
<212> TYPE: PRT
<213> ORGANISM: Homo sapiens

<400> SEQUENCE: 30

```
Met Leu Arg Ala Ala Ala Arg Phe Gly Pro Arg Leu Gly Arg Arg Leu
1               5                   10                  15

Leu Ser Ala Ala Ala Thr Gln Ala Val Pro Ala Pro Asn Gln Gln Pro
            20                  25                  30

Glu Val Phe Cys Asn Gln Ile Phe Ile Asn Asn Glu Trp His Asp Ala
        35                  40                  45

Val Ser Arg Lys Thr Phe Pro Thr Val Asn Pro Ser Thr Gly Glu Val
    50                  55                  60

Ile Cys Gln Val Ala Glu Gly Asp Lys Glu Asp Val Asp Lys Ala Val
65                  70                  75                  80

Lys Ala Ala Arg Ala Ala Phe Gln Leu Gly Ser Pro Trp Arg Arg Met
                85                  90                  95

Asp Ala Ser His Arg Gly Arg Leu Leu Asn Arg Leu Ala Asp Leu Ile
            100                 105                 110

Glu Arg Asp Arg Thr Tyr Leu Ala Ala Leu Glu Thr Leu Asp Asn Gly
        115                 120                 125

Lys Pro Tyr Val Ile Ser Tyr Leu Val Asp Leu Asp Met Val Leu Lys
    130                 135                 140

Cys Leu Arg Tyr Tyr Ala Gly Trp Ala Asp Lys Tyr His Gly Lys Thr
145                 150                 155                 160

Ile Pro Ile Asp Gly Asp Phe Phe Ser Tyr Thr Arg His Glu Pro Val
                165                 170                 175

Gly Val Cys Gly Gln Ile Ile Pro Trp Asn Phe Pro Leu Leu Met Gln
            180                 185                 190

Ala Trp Lys Leu Gly Pro Ala Leu Ala Thr Gly Asn Val Val Val Met
        195                 200                 205

Lys Val Ala Glu Gln Thr Pro Leu Thr Ala Leu Tyr Val Ala Asn Leu
    210                 215                 220

Ile Lys Glu Ala Gly Phe Pro Pro Gly Val Val Asn Ile Val Pro Gly
225                 230                 235                 240

Phe Gly Pro Thr Ala Gly Ala Ala Ile Ala Ser His Glu Asp Val Asp
                245                 250                 255

Lys Val Ala Phe Thr Gly Ser Thr Glu Ile Gly Arg Val Ile Gln Val
            260                 265                 270

Ala Ala Gly Ser Ser Asn Leu Lys Arg Val Thr Leu Glu Leu Gly Gly
        275                 280                 285
```

Lys Ser Pro Asn Ile Ile Met Ser Asp Ala Asp Met Asp Trp Ala Val
            290                 295                 300

Glu Gln Ala His Phe Ala Leu Phe Phe Asn Gln Gly Gln Cys Cys Cys
305                 310                 315                 320

Ala Gly Ser Arg Thr Phe Val Gln Glu Asp Ile Tyr Asp Glu Phe Val
                325                 330                 335

Glu Arg Ser Val Ala Arg Ala Lys Ser Arg Val Val Gly Asn Pro Phe
            340                 345                 350

Asp Ser Lys Thr Glu Gln Gly Pro Gln Val Asp Glu Thr Gln Phe Lys
                355                 360                 365

Lys Ile Leu Gly Tyr Ile Asn Thr Gly Lys Gln Glu Gly Ala Lys Leu
    370                 375                 380

Leu Cys Gly Gly Gly Ile Ala Ala Asp Arg Gly Tyr Phe Ile Gln Pro
385                 390                 395                 400

Thr Val Phe Gly Asp Val Gln Asp Gly Met Thr Ile Ala Lys Glu Glu
                405                 410                 415

Ile Phe Gly Pro Val Met Gln Ile Leu Lys Phe Lys Thr Ile Glu Glu
            420                 425                 430

Val Val Gly Arg Ala Asn Asn Ser Thr Tyr Gly Leu Ala Ala Ala Val
                435                 440                 445

Phe Thr Lys Asp Leu Asp Lys Ala Asn Tyr Leu Ser Gln Ala Leu Gln
450                 455                 460

Ala Gly Thr Val Trp Val Asn Cys Tyr Asp Val Phe Gly Ala Gln Ser
465                 470                 475                 480

Pro Phe Gly Gly Tyr Lys Met Ser Gly Ser Gly Arg Glu Leu Gly Glu
                485                 490                 495

Tyr Gly Leu Gln Ala Tyr Thr Glu Val Lys Thr Val Thr Val Lys Val
                500                 505                 510

Pro Gln Lys Asn Ser
        515

<210> SEQ ID NO 31
<211> LENGTH: 21
<212> TYPE: DNA
<213> ORGANISM: Homo sapiens

<400> SEQUENCE: 31
tcacagtgaa ccggtctctt t                                                 21

<210> SEQ ID NO 32
<211> LENGTH: 21
<212> TYPE: DNA
<213> ORGANISM: Homo sapiens

<400> SEQUENCE: 32
ttcacagtgg ctaagttccg c                                                 21

<210> SEQ ID NO 33
<211> LENGTH: 21
<212> TYPE: DNA
<213> ORGANISM: Homo sapiens

<400> SEQUENCE: 33
ttcacagtgg ctaagttctg c                                                 21

<210> SEQ ID NO 34
<211> LENGTH: 22

```
<212> TYPE: DNA
<213> ORGANISM: Homo sapiens

<400> SEQUENCE: 34
taatactgcc tggtaatgat ga                                    22

<210> SEQ ID NO 35
<211> LENGTH: 23
<212> TYPE: DNA
<213> ORGANISM: Homo sapiens

<400> SEQUENCE: 35
taatactgcc gggtaatgat gga                                   23

<210> SEQ ID NO 36
<211> LENGTH: 22
<212> TYPE: DNA
<213> ORGANISM: Homo sapiens

<400> SEQUENCE: 36
taatactgtc tggtaaaacc gt                                    22

<210> SEQ ID NO 37
<211> LENGTH: 22
<212> TYPE: DNA
<213> ORGANISM: Homo sapiens

<400> SEQUENCE: 37
gcctgctggg gtggaacctg gt                                    22

<210> SEQ ID NO 38
<211> LENGTH: 22
<212> TYPE: DNA
<213> ORGANISM: Homo sapiens

<400> SEQUENCE: 38
attctgcatt tttagcaagt tc                                    22

<210> SEQ ID NO 39
<211> LENGTH: 21
<212> TYPE: DNA
<213> ORGANISM: Homo sapiens

<400> SEQUENCE: 39
taaagtgctg acagtgcaga t                                     21

<210> SEQ ID NO 40
<211> LENGTH: 22
<212> TYPE: DNA
<213> ORGANISM: Homo sapiens

<400> SEQUENCE: 40
caaagtgcct cccttttagag tg                                   22

<210> SEQ ID NO 41
<211> LENGTH: 23
<212> TYPE: DNA
<213> ORGANISM: Homo sapiens

<400> SEQUENCE: 41
aaaagtgctt acagtgcagg tag                                   23

<210> SEQ ID NO 42
```

```
<211> LENGTH: 23
<212> TYPE: DNA
<213> ORGANISM: Homo sapiens

<400> SEQUENCE: 42
caaagtgctt acagtgcagg tag                                              23

<210> SEQ ID NO 43
<211> LENGTH: 23
<212> TYPE: DNA
<213> ORGANISM: Homo sapiens

<400> SEQUENCE: 43
taaagtgctt atagtgcagg tag                                              23

<210> SEQ ID NO 44
<211> LENGTH: 23
<212> TYPE: DNA
<213> ORGANISM: Homo sapiens

<400> SEQUENCE: 44
caaagtgctc atagtgcagg tag                                              23

<210> SEQ ID NO 45
<211> LENGTH: 23
<212> TYPE: DNA
<213> ORGANISM: Homo sapiens

<400> SEQUENCE: 45
caaagtgctg ttcgtgcagg tag                                              23

<210> SEQ ID NO 46
<211> LENGTH: 22
<212> TYPE: DNA
<213> ORGANISM: Homo sapiens

<400> SEQUENCE: 46
tgtaacagca actccatgtg ga                                               22

<210> SEQ ID NO 47
<211> LENGTH: 22
<212> TYPE: DNA
<213> ORGANISM: Homo sapiens

<400> SEQUENCE: 47
tgtgactggt tgaccagagg gg                                               22

<210> SEQ ID NO 48
<211> LENGTH: 22
<212> TYPE: DNA
<213> ORGANISM: Homo sapiens

<400> SEQUENCE: 48
tggaatgtaa ggaagtgtgt gg                                               22

<210> SEQ ID NO 49
<211> LENGTH: 22
<212> TYPE: DNA
<213> ORGANISM: Homo sapiens

<400> SEQUENCE: 49
agatcagaag gtgattgtgg ct                                               22
```

```
<210> SEQ ID NO 50
<211> LENGTH: 22
<212> TYPE: DNA
<213> ORGANISM: Homo sapiens

<400> SEQUENCE: 50
gagggttggg tggaggctct cc                                              22

<210> SEQ ID NO 51
<211> LENGTH: 22
<212> TYPE: DNA
<213> ORGANISM: Homo sapiens

<400> SEQUENCE: 51
tatgtgggat ggtaaaccgc tt                                              22

<210> SEQ ID NO 52
<211> LENGTH: 22
<212> TYPE: DNA
<213> ORGANISM: Homo sapiens

<400> SEQUENCE: 52
agtggggaac ccttccatga gg                                              22
```